United States Patent
Sangita et al.

(10) Patent No.: US 7,427,686 B2
(45) Date of Patent: Sep. 23, 2008

(54) (3R, 4R)-TRANS-3, 4-DIARYLCHROMAN DERIVATIVES AND A METHOD FOR THE PREVENTION AND/OR TREATMENT OF ESTROGEN DEPENDENT DISEASES

(75) Inventors: Sangita, Lucknow (IN); Atul Kumar, Lucknow (IN); Man Mohan Singh, Lucknow (IN); Suprabhat Ray, Lucknow (IN); Girish Kumar Jain, Lucknow (IN)

(73) Assignee: Counsel of Scientific and Industrial Research, New Delhi (IN)

( * ) Notice: Subject to any disclaimer, the term of this patent is extended or adjusted under 35 U.S.C. 154(b) by 246 days.

(21) Appl. No.: 10/677,116

(22) Filed: Sep. 30, 2003

(65) Prior Publication Data

US 2005/0070597 A1   Mar. 31, 2005

(51) Int. Cl.
C07D 311/00 (2006.01)
(52) U.S. Cl. ...................... 549/406; 514/456
(58) Field of Classification Search ................ 549/406; 546/196; 544/151, 376; 548/525; 514/456, 514/422, 320, 254.11, 233.5
See application file for complete search history.

(56) References Cited

U.S. PATENT DOCUMENTS 5,985,306 A * 11/1999 Jacobsen et al. ............ 424/423
5,994,390 A * 11/1999 Jacobsen et al. ............ 514/422
6,043,269 A *  3/2000 Jacobsen et al. ............ 514/422
6,316,494 B1* 11/2001 Jacobsen et al. ............ 514/456

OTHER PUBLICATIONS

Verma, P et al 'Mechanism of action of nonsteroidal antiestrogens: a possible link with antiinflammatory activity' CA 111:224813 (1989).*
Branham, Phytoestrogens and mycoestrogens bind to the rat uterine estrogen receptor, J. Nutr. 132:658-664, (2002).*
Tripathi et al. STN Accession No. 2005:412580;Document No. 142:411230;abstract of the IN 186459, Filing date Sep. 1, 2001.*
Verma et al. STN Accession No. 1989:624813; Document No. 111:224813; abstract of (Indian Journal of Pharmaceutical Sciences, 1989, 51(2), 48-50).*
Johnston et al., "Idoxifene Antagonizes Estradiol-dependent MCF-7 Breast Cancer Xenograft Growth through Sustained Induction of Apoptosis," *Cancer Research*, vol. 59, pp. 3646-3651, Aug. 1, 1999.
Jordan, et al, "Determination and Pharmacology of an New Hydroxylated Metabolite of Tamoxifen Observed in Patient Sera during Therapy for Advanced Breast Cancer," *Cancer Research*, vol. 43, pp. 1446-1450, Mar. 1983.
Blair et al., "The Estrogen Receptor Relative Binding Affinities of 188 Natural and Xenochemicals: Structural Diversity of Ligands," *Toxicology Sciences*, vol. 54, pp. 138-153 (2000).

* cited by examiner

*Primary Examiner*—D. Margaret Seaman
*Assistant Examiner*—Nizal S Chandrakumar
(74) *Attorney, Agent, or Firm*—Edwards Angell Palmer & Dodge LLP; Jun Umemuro; Gregory B. Butler, Esq.

(57) ABSTRACT

The present invention relates to compounds of the formula I in which substituents $R^2$ and $R^3$ are arranged in trans-configuration:

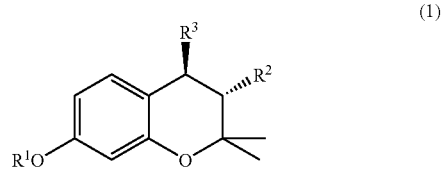

(1)

wherein:
$R^1$ is H or C1-C6 alkyl; C3-C7 cycloalkyl;
$R^2$ is phenyl, optionally substituted with 1 to 5 substituents independently selected from the group comprising OH, C1-C6-alkyl, halogen, nitro, cyano, SH, $SR^4$, trihalo-C1-C6-alkyl, C1-C6-alkoxy and phenyl, wherein $R^4$ is C1-C6 alkyl;
$R^3$ is phenyl substituted with $OR^5$ wherein $R^5$ has the formula (II), (III) or (IV)

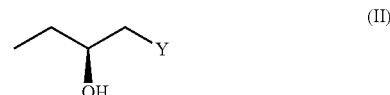

(II)

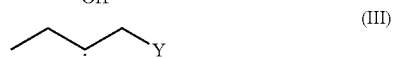

(III)

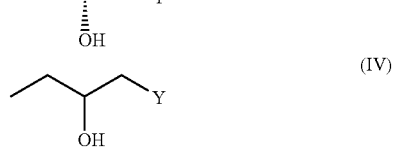

(IV)

wherein Y is chosen from $NHR^4$, $NR^4{}_2$, $NHCOR^4$, $NHSO_2R^4$, $CONHR^4$, $CONR^4$, $CONR^4{}_2$, COOH, $COOR^4$, $SO_2R^4$, $SOR^4$, $SONHR^4$, $SONR^4{}_2$, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, $SR^4$, trihalo-C1-C6-alkyl, C1-C6-alkyl and C1-C6-alkoxy, preferably $NHR^4$, $NR_2{}^4$, or a nitrogen heterocycle, wherein $R^4$ is as defined above, and the esters, ethers, and salts of the compounds of formula I, optionally along pharmaceutically acceptable excipients, a process for the preparation of the same, and a method of preventing and/or treating estrogen-related disease conditions in a subject using compounds of formula 1, or its salts, optionally along with pharmaceutically acceptable excipients.

2 Claims, No Drawings

(3R, 4R)-TRANS-3, 4-DIARYLCHROMAN DERIVATIVES AND A METHOD FOR THE PREVENTION AND/OR TREATMENT OF ESTROGEN DEPENDENT DISEASES

FIELD OF THE PRESENT INVENTION

The present invention relates to compounds of the formula I in which substituents $R^2$ and $R^3$ are arranged in trans-configuration:

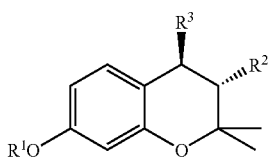

(1)

wherein,
$R^1$ is H or C1-C6 alkyl; C3-C7 cycloalkyl; $R^2$ is phenyl, optionally substituted with 1 to 5 substituents independently selected from the group comprising OH, C1-C6-alkyl, halogen, nitro, cyano, SH, $SR^4$, trihalo-C1-C6-alkyl, C1-C6-alkoxy and phenyl, wherein $R^4$ is C1-C6 alkyl; $R^3$ is phenyl substituted with $OR^5$ wherein $R^5$ has the formula (II), (III) or (IV)

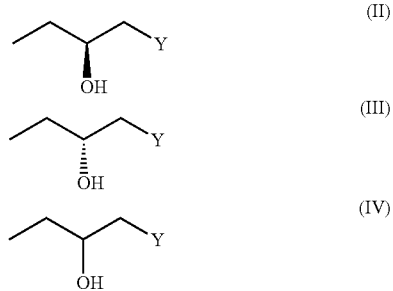

wherein Y is chosen from $NHR^4$, $NR^4_2$, $NHCOR^4$, $NHSO_2R^4$, $CONHR^4$, $CONR^4$, $CONR^4_2$, COOH, $COOR^4$, $SO_2R^4$, $SOR^4$, $SONHR^4$, $SONR^4_2$, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, $SR^4$, trihalo-C1-C6-alkyl, C1-C6-alkyl and C1-C6-alkoxy, preferably $NHR^4$, $NR^4_2$, or a nitrogen heterocycle, wherein $R^4$ is as defined above, and the esters, ethers, and salts of the compounds of formula I, optionally along with pharmaceutically acceptable excipients, a process for the preparation of the same, and a method of preventing and/or treating estrogen-related disease conditions in a subject using compounds of formula 1, or its salts, optionally along with pharmaceutically acceptable excipients.

BACKGROUND OF THE PRESENT INVENTION

Menopause in women's life is the most critical stage of the life when she undergoes dramatic physiological changes and is defined as the transition in women from reproductive to non-reproductive stage of life, which is due to the cessation of menstruation and occurs at an average age of fifty years. More particularly, the post-menopausal stage is characterized by the changes in the levels of circulating sex hormones, the most dramatic of which is the reduction in plasma levels of 17-beta-estradiol to less than ten percent of pre-menopausal values, which results in a number of chronic disorders and is often referred to as Post Menopausal Syndrome. In view of the fact that the current life span of women is about eighty years, women spend approximately one-third of their lives in the post-menopausal state. This means that the potential for chronic effects of the post-menopausal state on women's health is far greater today than at the turn of the century when life expectancy was considerably shorter.

Estrogen deficiency is the most important risk factor associated with Post Menopausal Syndrome. Some of the major effects of the Post Menopausal Syndrome that are source of greatest long-term medical concern include osteoporosis, bone loss, bone formation, cardiovascular effects more particularly hyperlipidaemia, thrombosis and vasomotor disorders, neurodegenerative effects such as stroke, senile dementia-Alzheimer type and Parkinson disease, menopausal symptoms including hot flushes, urogenital atrophy, depression, mania, schizophrenia, urinary incontinence, relief of dysmenorrhea; relief of dysfunctional uterine bleeding, an aid in ovarian development, treatment of acne, hirsutism.

Osteoporosis can be defined as a reduction in bone mass per unit volume with an alteration in bone microarchitecture that results in an increased susceptibility to fractures. It is not surprising that the most common fractures are those associated with bones, which are highly dependent on trabecular support, for example the vertebrae, the neck, and the weight bearing bone such as the femur, and the fore arm. Indeed the hip fracture, collies fractures and vertebrae crush fractures are hallmarks of post-menopausal osteoporosis. In most cases, bone loss occurs as a result of increased bone destruction (resorption) relative to bone formation and most women lose from about 20% to 60% of the bone mass in the trabecular compartment of the bone within 3 to 6 years after the menopause.

Osteoporosis, more particularly the post-menopausal osteoporosis represents a major problem in women health care and poses a risk to quality of life during old age. Efforts to reduce this risk factor and incidence of fractures have resulted in the development of compounds that conserve skeletal mass by inhibiting bone resorption and/or by enhancing bone formation (Dwivedi I, Ray S, 1995 "Recent developments in the chemotherapy of osteoporosis" Progress in Drug Research 45, 289-338, Editor E Jucker, Birkhauser Vela; Marshall D H, Horsmann A, Nordin B E C, 1977, "The prevention and management of post-menopausal osteoporosis" Acta Obstet Gynecol Scand (Suppl) 65:49-56; Hutchinson T A, Polansky S M, Feinstein A R, 1979, "Postmenopausal estrogen protect against fractures of hip and distal radius: A care-control study" Lancet 2:705-709. Estrogen replacement therapy also has positive effect on CVS & CNS related disorders (Lobo R A, 1990, "Cardiovascular implication of estrogen replacement therapy" Obstetrics & Gynaecology 75:185-245; Mendelson M E, Karas R H, 1994, "Estrogen and the blood vessel wall" Current opinion in Cardiology 1994:619-626; Stampfer M J, Colditz G A, 1991, "Estrogen replacement therapy and coronary heart disease: a quantitative assessment of the epidemiological evidence" Preventive Medicine 20:47-63).

Cardiovascular disease is another leading cause of morbidity and mortality in older women. Menopause and ageing increase risk of atherosclerosis and coronary artery disease.

An altered lipid profile is thought to be associated with this increased risk. Compared to men, pre-menopausal women are relatively more protected from cardiovascular diseases. This protection is gradually lost following menopause. This loss of protection has been linked to the loss of estrogen and in particular to the loss of estrogen's stationary phase ability to regulate the level of serum lipids. The nature of estrogens ability to reduce serum lipids is not well understood, but evidences indicate that estrogen can up-regulate LDL receptors in the liver which act to remove excess cholesterol.

Additionally, estrogen appears to have some effects on the biosynthesis of cholesterol and other beneficial effects on cardiovascular health. Estrogen is also believed to directly influence vessel wall compliance, reduce peripheral resistance and prevent atherosclerosis. It is also reported that serum lipids in post-menopausal women having estrogen replacement therapy (ERT) return to concentrations found in the pre-menopausal state (Gruber C J, Tschugguel W, Schneeberger C, Huber J C, 2002, "Production and actions of estrogens" The New England Journal of Medicine 346:340-352; Bellino F L, Wise P M, 2003 "Nonhuman primate models of menopause workshop" Biology of Reproduction 68:10-18; Lobo R A 1990, "Cardiovascular implication of estrogen replacement therapy", Obstetrics and Gynaecology 75:18S-24S; Medelson M E, Karas R D 1994, "Estrogen and the blood vessel wall", Current opinion in Cardiology, 1994 (9): 619-626).

Based on available epidemiological data, the overall impact of these physiological and pharmacological actions of estrogen is an age independent reduction in cardiovascular mortality and morbidity in women (Knnel W H, Hjortland M, McNamara P M, 1976 "Menopause and risk of cardiovascular disease: The Framingham Study", Ann Int Med 8:5447-5552). Furthermore, a more recent analysis has concluded that post-menopausal estrogen replacement therapy reduces the risk of cardiovascular disease by approximately 50 percent (Stampfer M J, Colditz G A, 1991, "Estrogen replacement therapy and coronary heart disease: a quantitative assessment of the epidemiological evidence", Preventive Medicine 20:47-63).

There is growing interest in recent years on neuroprotective effects of estrogens for neurodegenerative conditions such as stroke, Alzheimer disease and Parkinson disease. Reports of greater brain damage in males than in females and in ovariectomized than intact female animals in ischemic stroke models are available. Estrogen is also known to increase density of N-methyl-D-aspartate receptors and increase neuronal sensitivity to input mediated by these receptors in neurons of hippocampus, the area involved in memory. The estradiol-depleted state in post-menopausal women has been correlated with increased incidence of stroke, cognitive defects, hot flashes, mood changes, and early onset and severity of Alzheimer disease. Some epidemiological data suggests that in post-menopausal women, estrogen deficiency is associated with decline in cognitive function and increased risk of Alzheimer's disease (Gruber C J, Tschugguel W, Schneeberger C, Huber J C, 2002 "Production and actions of estrogens", The New England Journal of Medicine 346:340-352; Dhandapani K M, Brann D W, 2002, "Protective effects of estrogen and Selective Estrogen Receptor Modulators in the brain" Biology of Reproduction 67:1379-1385).

Short-term studies in human subjects have shown that increased levels of estrogen are associated with higher memory scores in post-menopausal women (Kampen D L, Sherwin B B, 1994 "Estrogen use and verbal memory in healthy postmenopausal women", Obstetrics & Gynaecology 83:979-983; Ohkura T, Isse K, Akazawa K, Hamanioto M, Yoshimasa Y, Hagino N, 1995, "Long-term estrogen replacement therapy in female patients with dementia of the Alzheimer Type: 7 Case reports", Dementia 6:99-107). Furthermore, the administration of exogenous estrogen to surgically post-menopausal women specially enhances short-term memory. Moreover, the effects as epidemiological findings indicate that estrogen treatment significantly decreases the risk of senile dementia-Alzheimer type in women (Paganini-Hill A, Henderson V W, 1994, "Estrogen deficiency and risk of Alzheimer's disease in women", Am J Epidemiol 140:256-261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia 6:99-107).

While the mechanism whereby estrogens enhance cognitive function is unknown, it is possible to speculate that the direct effects of estrogen on cerebral blood flow (Goldman H, Skelley E b, Sandman C A, Kastin A J, Murphy S, 1976, "Hormones and regional brain blood flow", Pharmacik Biochem Rev 5 (suppl 1):165-169; Ohkura T, Teshima Y, Isse K, Mastuda H, Inoue T, Sakai Y, Iwasaki N, Yaoi Y, 1995, "Estrogen increases cerebral and cerebellar blood flows in post-menopausal women", Menopause: J North Am Menopause Soc 2:13-18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology 136:2320-2324; McMillan P J, Singer C A, Dorsa D M, 1996, "The effects of ovariectomy and estrogen replacement on trkA and choline acetyltransferase mRNA expression in the basal forebrain of the adult female Sprague-Dawley rat", Neurosci 16:1860-1865).

Even though the beneficial effects of estrogen replacement on a wide variety of organ systems and tissues appear indisputable, the dose and duration of estrogen therapy is also associated with an increased risk of endometrial hyperplasia and carcinoma. The use of concomitant cyclic progestins does reduce the risk of endometrial pathology, but this is achieved at the expense of the return of regular uterine bleeding, a result that is objectionable to many patients. In addition to estrogen's stimulatory effect on the endometrium, there remains considerable controversy regarding reports of an association between long-term estrogen replacement and an increased risk of breast cancer (Bergkvist L, Adami H O, Persson I, Hoover R, Schairer C, 1989, "The risk of breast cancer after estrogen and estrogen-progestin replacement", N Eng J Med, 321:293-297; Coiditz G A, Hankinson S E, Hunter D J, Willett W X, Manson J E, Stampfer M J, Hennekens C, Rosner B, Speizer F E, 1995, "The use of estrogens and progestins and the risk of breast cancer in postmenopausal women", N Eng J Med 332:1593). Furthermore, there are other side effects of estrogen replacements, which, while might not be life threatening, contraindicate estrogen's use and reduce patient compliance.

Breast cancer is by far the most common malignant disease in women (22% of all new cancer cases). Concerted efforts are being made worldwide to develop new and safer drugs for the treatment of breast cancer. Tamoxifen ('Nolvadex'), a selective estrogen receptor modulator (SERM), is currently the most widely used drug for the treatment of estrogen receptor positive (ER+ve) breast cancer. Tamoxifen inhibits the estrogen-dependent growth of cancer cells by competitive binding to estrogen receptors of the cells. However, as tamoxifen has also estrogen-like effects, it induces, among other adverse effects, endometrial cancer, deep vein thrombosis and pulmonary embolism in women undergoing the therapy. In addition, tamoxifen is known to induce DNA adduct formation and produced liver tumors in rodent life-term bioassays. Thus there is an urgent need for developing safer SERMs for the treatment of breast cancer (Baum M, Odling-Smee W, Houghton J, Riley D, Taylor H, 1994, "Endometrial cancer during tamoxifen treatment", Lancet 343:1291; Clemons M, Danson S, Howell A, 2002, "Tamoxifen ('Nolvadex'): Antitumour treatment. A review", Cancer Treatment Reviews 28:165-180; Huggins, C, Yang N C, 1962, "Induction and extinction of mammary cancer", Science 137:257-262; Williams G M, Latropoulos, M J, Djordjevic M V, Kaltenberg O P, 1993, "The triphenylethylene drug tamoxifen is a strong liver carcinogen in the rat", Carcinogenesis 14:315-317; Meier C R, Jick H, 1998, "Tamoxifen and risk of idiopathic venous thromboembolism", Br J Clin Pharmacol 45:608-612).

Egg-implantation in most mammals is dependent on a sequential action of estrogen and progesterone on the uterus and is considered as a preferential peripheral site for contraception. Development of hormone antagonists (both antiestrogens and antiprogestins) which inhibit action of endogenous hormones at the receptor level resulting in inhibition of implantation is one of the promising approaches for control or regulation of fertility in humans and other animals. Previous studies have revealed that administration of estrogen antagonists, recently termed as Selective Estrogen Receptor Modulators (SERMs), due to their tissue selective action) to cyclic or mated females prevents implantation.

Studies also reveal their uterine specific action, inhibiting endometrial receptivity to embryonic signal(s) for decidualisation, without affecting pre-implantation development of embryos up to the blastocyst stage (Singh M M, 2001, "Centchroman, a selective estrogen receptor modulator, as contraceptive and in the management of hormone related clinical disorders", Medicinal Research Reviews 21:302-347; Nityanand S, Chandravati, Singh L, Srivastava J S, Kamboj V P, 1988, "Clinical evaluation of centchroman: A new oral contraceptive", In: Hormone Antagonists for Fertility Regulation, Eds Puri C P, Van Look P FA, Indian Society for the Study of Reproduction and Fertility, Bombay, India, 223-230; Puri V, Kamboj V P, Chandra H, Ray S, Kole P L, Dhawan B N, Anand N, 1988, "Results of multicentric trial of centchroman", In: Pharmacology for Health in Asia, Eds Dhawan B N, Agarwal K K, Arora R B, Parmar S S, Allied Publishers, New Delhi, 439-447; Nityanand S, Kamboj V P, Chandravati, Das K, Gupta K, Rohtagi P, Baveja R, Jina R, Mitra R, Sharma U, 1994, "Contraceptive efficacy and safety of centchroman with biweekly-cum-weekly schedule", In: Current Concepts in Fertility Regulation and Reproduction, Eds Puri C P, Van Look P FA, Wiley Eastern Ltd., New Delhi, 61-68; Nityanand S, Gupta R C, Kamboj V P, Srivastava P K, Berry M, 1995, "Centchroman: Current Status as a contraceptive", Indian Progress in Family Welfare 10:26-31; Nityanand S, Anand N, 1996, "Centchroman: A nonsteroidal antifertility agent", FOGSI FOCUS, March issue: 8-10).

Such SERMs have also been successfully used for induction of ovulation in amenorrhic women under the assisted reproduction programmes (Roy S N, Kumari G L, Modoiya K, Prakash V, Ray S, 1976, "Induction of ovulation in human with centchroman, a preliminary report", Fertility and Sterility 27:1108-1110) and suppression of post-partum lactation (Goodman and Gilman, The Pharmacological Basis of Therapeutics (Seventh Edition) Macmillan Publishing Company, 1985, pages 1321-1423).

From the foregoing discussion it would appear that the availability of therapies which possess the ideal pharmacological profile and could mimic the beneficial actions of estrogen on the bone, cardiovascular system and central nervous system without the undesirable side effects on uterus and breast, would essentially provide a "safe estrogen" which could dramatically influence the number of patients that would be able to benefit from estrogen replacement therapy. Therefore, in recognition of estrogen's beneficial effects on a number of body systems and disease conditions, there is a continuing need for the development of potent estrogen agonists which can selectively target different body tissues. Accordingly, the present invention provides new compounds, pharmaceutically acceptable salts and compositions thereof and methods of using such compounds for the prevention or treatment of:

(a) estrogen deficient or deprivation state in a mammal, in particular osteoporosis, bone loss, bone formation, cardiovascular effects more particularly hyperlipidaemia, thrombosis and vasomotor system, neurodegenerative effects such as stroke, senile dementia-Alzheimer type and Parkinson disease, menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism;

(b) estrogen dependent or estrogen independent cancers such as prostatic carcinoma, cancer of breast, cancer of uterus, cancer of the cervix and cancer of the colon;

(c) an aid in ovarian development or function;

(d) control or regulation of fertility in humans and in other animals;

(e) prevention of threatened or habitual abortion;

(f) suppression of post-partum lactation;

(g) physiological disorders such as obesity, depression etc.;

(h) regulation of glucose metabolism in non-insulin dependent diabetes mellitus.

OBJECTS OF THE PRESENT INVENTION

The main object of the present invention is to develop compounds of the formula I in which substituents $R^2$ and $R^3$ are arranged in trans-configuration:

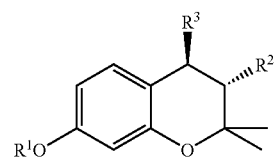

(1)

wherein,
$R^1$ is H or C1-C6 alkyl; C3-C7 cycloalkyl; $R^2$ is phenyl, optionally substituted with 1 to 5 substituents independently selected from the group comprising OH, C1-C6-alkyl, halogen, nitro, cyano, SH, $SR^4$, trihalo-C1-C6-alkyl, C1-C6-alkoxy and phenyl, wherein $R^4$ is C1-C6 alkyl; $R^3$ is phenyl substituted with $OR^5$ wherein $R^5$ has the formula (II), (III) or (IV)

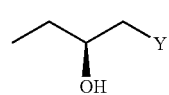

(II)

-continued

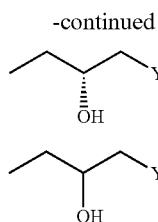

wherein Y is chosen from NHR⁴, NR⁴₂, NHCOR⁴, NHSO₂R⁴, CONHR⁴, CONR⁴, CONR⁴₂, COOH, COOR⁴, SO₂R⁴, SOR⁴, SONHR⁴, SONR⁴₂, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, SR⁴, trihalo-C1-C6-alkyl, C1-C6-alkyl and C1-C6-alkoxy, preferably NHR⁴, NR₂⁴, or a nitrogen heterocycle, wherein R⁴ is as defined above, and the esters, ethers, and salts of the compounds of formula I, optionally along pharmaceutically acceptable excipients.

Another main object of the present invention is to develop a process for the preparation of compounds of formula I.

Yet another object of the present invention is to develop a method of preventing and/or treating estrogen-related disease conditions in a subject in need thereof, said method comprising step of administering to the subject, a pharmaceutically effective amount of compounds of formula 1, or its salts, optionally along with pharmaceutically acceptable excipients.

Still another object of the present invention is to develop a method of preventing and/or treating estrogen-related disease conditions in a subject in need thereof, wherein said method helps in preferably diseases or syndromes caused by an estrogen-deficient state, with Relative Binding affinity (RBA) to estrogen receptors ranging between 5 to 7.

Still another object of the present invention is to develop a method of preventing and/or treating estrogen-related disease conditions in a subject in need thereof, wherein said method helps in disease conditions caused by osteoprosis, bone loss and bone formation, with T/C ratio of ≦0.6.

Still another object of the present invention is to develop a method of preventing and/or treating estrogen-related disease conditions in a subject in need thereof, wherein said method helps in disease conditions affecting cardiovascular systems, more particularly hyperlipidaemia, thrombosis and vasomotor system.

Still another object of the present invention is to develop a method to help in disease conditions showing neurodegenerative effects, more particularly, stroke, senile dementia-Alzheimer type and Parkinson disease.

Still another object of the present invention is to develop a method to help in disease conditions showing menopausal symptoms, more particularly, hot flushes, urogenital atrophy, depression, mania, schizophrenia, urinary incontinence, dysmenorrhea, dysfunctional uterine bleeding, acne, hirsutism, improper ovarian development.

Still another object of the present invention is to develop a method to help in disease conditions showing cancers, more particularly, prostatic carcinoma, breast cancer, cancer of uterus, cancer of the cervix and colon cancer, with LC₅₀ ranging between 17 to 20 μM.

Still another object of the present invention is to develop a method wherein the volume of the tumor decreases by about 25%.

Still another object of the present invention is to develop method to help regulate fertility in humans and in other animals.

Still another object of the present invention is to develop a method to help in threatened or habitual abortion.

Still another object of the present invention is to develop a method to help in suppression of post-partum lactation.

Still another object of the present invention is to develop a method to help in the management of certain physiological disorders, more particularly, obesity and depression.

Still another object of the present invention is to develop a method to help regulate of glucose metabolism in non-insulin dependent diabetes mellitus.

SUMMARY OF THE PRESENT INVENTION

The present invention relates to compounds of the formula I in which substituents R² and R³ are arranged in trans-configuration:

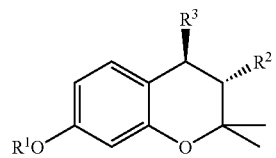

wherein:
R¹ is H or C1-C6 alkyl; C3-C7 cycloalkyl;
R² is phenyl, optionally substituted with 1 to 5 substituents independently selected from the group comprising OH, C1-C6-alkyl, halogen, nitro, cyano, SH, SR⁴, trihalo-C1-C6-alkyl, C1-C6-alkoxy and phenyl, wherein R⁴ is C1-C6 alkyl;
R³ is phenyl substituted with OR⁵ wherein R⁵ has the formula (II), (III) or (IV)

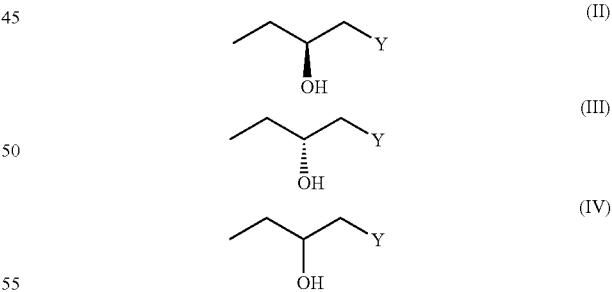

wherein Y is chosen from NHR⁴, NR⁴₂, NHCOR⁴, NHSO₂R⁴, CONHR⁴, CONR⁴, CONR⁴₂, COOH, COOR⁴, SO₂R⁴, SOR⁴, SONHR⁴, SONR⁴₂, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, SR⁴, trihalo-C1-C6-alkyl, C1-C6-alkyl and C1-C6-alkoxy, preferably NHR⁴, NR₂⁴, or a nitrogen heterocycle, wherein R⁴ is as defined above, and the esters, ethers, and salts of the compounds of formula I, optionally along with pharmaceutically acceptable excipients, a process for the preparation of the same, and a method of preventing and/or treating estrogen-related disease conditions in a subject using compounds of formula 1, or its salts, optionally along with pharmaceutically acceptable excipients.

DETAILED DESCRIPTION OF THE PRESENT INVENTION

Accordingly, the present invention relates to compounds of the formula I in which substituents $R^2$ and $R^3$ are arranged in trans-configuration:

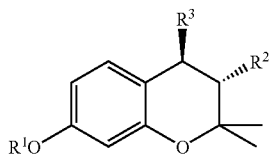

(1)

wherein:
$R^1$ is H or C1-C6 alkyl; C3-C7 cycloalkyl;
$R^2$ is phenyl, optionally substituted with 1 to 5 substituents independently selected from the group comprising OH, C1-C6-alkyl, halogen, nitro, cyano, SH, $SR^4$, trihalo-C1-C6-alkyl, C1-C6-alkoxy and phenyl, wherein $R^4$ is C1-C6 alkyl;
$R^3$ is phenyl substituted with $OR^5$ wherein $R^5$ has the formula (II), (III) or (IV)

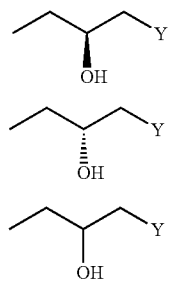

(II)

(III)

(IV)

wherein Y is chosen from $NHR^4$, $NR^4{}_2$, $NHCOR^4$, $NHSO_2R^4$, $CONHR^4$, $CONR^4$, $CONR^4{}_2$, COOH, $COOR^4$, $SO_2R^4$, $SOR^4$, $SONHR^4$, $SONR^4{}_2$, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, $SR^4$, trihalo-C1-C6-alkyl, C1-C6-alkyl and C1-C6-alkoxy, preferably $NHR^4$, $NR_2{}^4$, or a nitrogen heterocycle, wherein $R^4$ is as defined above, and the esters, ethers, and salts of the compounds of formula I, optionally along with pharmaceutically acceptable excipients, a process for the preparation of the same, and a method of preventing and/or treating estrogen-related disease conditions in a subject using compounds of formula 1, or its salts, optionally along with pharmaceutically acceptable excipients.

In the main embodiment of the present invention, the substituents $R^2$ and $R^3$ are arranged in trans-configuration in compounds of formula I, wherein compounds of the formula I in which substituents $R^2$ and $R^3$ are arranged in trans-configuration:

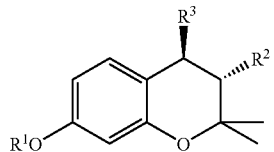

(1)

wherein:
$R^1$ is H or C1-C6 alkyl; C3-C7 cycloalkyl;
$R^2$ is phenyl, optionally substituted with 1 to 5 substituents independently selected from the group comprising OH, C1-C6-alkyl, halogen, nitro, cyano, SH, $SR^4$, trihalo-C1-C6-alkyl, C1-C6-alkoxy and phenyl, wherein $R^4$ is C1-C6 alkyl;
$R^3$ is phenyl substituted with $OR^5$ wherein $R^5$ has the formula (II), (III) or (IV)

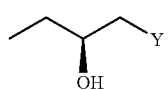

(II)

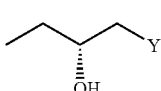

(III)

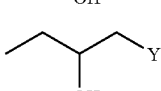

(IV)

wherein Y is chosen from $NHR^4$, $NR^4{}_2$, $NHCOR^4$, $NHSO_2R^4$, $CONHR^4$, $CONR^4$, $CONR^4{}_2$, COOH, $COOR^4$, $SO_2R^4$, $SOR^4$, $SONHR^4$, $SONR^4{}_2$, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, $SR^4$, trihalo-C1-C6-alkyl, C1-C6-alkyl and C1-C6-alkoxy, preferably $NHR^4$, $NR_2{}^4$, or a nitrogen heterocycle, wherein $R^4$ is as defined above, and the esters, ethers, and salts of the compounds of formula I, optionally along pharmaceutically acceptable excipients.

In another main embodiment of the present invention, wherein $R^3$ is phenyl substituted with —$OR^5$ wherein $R^5$ has the formula II and wherein Y is a C3-C7 heterocyclic ring, saturated or unsaturated, containing one or two heteroatoms independently selected from the group comprising O, S and N, optionally being substituted with 1 to 3 substituents independently selected from the group comprising H, OH, halogen, nitro, cyano, SH, $SR^4$, trihalo-C1-C6-alkyl, C1-C6-alkyl, C1-C6-alkyl and C1-C6-alkoxy.

In yet another main embodiment of the present invention, wherein $R^3$ is phenyl substituted with —$OR^5$ wherein $R^5$ has the formula III and wherein Y is a C3-C7 heterocyclic ring, saturated or unsaturated, containing one or two heteroatoms independently selected from the group comprising O, S and N, optionally being substituted with 1 to 3 substituents independently selected from the group comprising H, OH, halogen, nitro, cyano, SH, $SR^4$, trihalo-C1-C6-alkyl, C1-C6-alkyl, C1-C6-alkyl and C1-C6-alkoxy.

In still another main embodiment of the present invention, wherein $R^3$ is phenyl substituted with —$OR^5$ wherein $R^5$ has the formula IV and wherein Y is a C3-C7 heterocyclic ring, saturated or unsaturated, containing one or two heteroatoms independently selected from the group comprising O, S and N, optionally being substituted with 1 to 3 substituents independently selected from the group comprising H, OH, halogen, nitro, cyano, SH, $SR^4$, trihalo-C1-C6-alkyl, C1-C6-alkyl, C1-C6-alkyl and C1-C6-alkoxy.

In still another main embodiment of the present invention, wherein $R^1$ is preferably methyl.

In still another main embodiment of the present invention, wherein $R^2$ is preferably phenyl.

In still another main embodiment of the present invention, wherein $R^4$ is preferably butyl.

In still another main embodiment of the present invention, wherein the preferred compounds are:

a. (3R,4R)-2,2-Dimethyl-7-methoxy-4-(4-[{2R}-3-methylamino-2-hydroxy}propyloxy]phenyl)-3-phenylchroman.
b. (3R,4R)-2,2-Dimethyl-7-methoxy-4-(4-[{2R}-3-ethylamino-2-hydroxy}propyloxy]phenyl)-3-phenylchroman.
c. (3R,4R)-2,2-Dimethyl-7-methoxy-3-phenyl-4-(4-[{2R}-3-propylamino-2-hydroxy}propyloxy]phenyl)chroman.
d. (3R,4R)-4-(4-[{2R}-3-Butylamino-2-hydroxy}propyloxy]phenyl)-2,2-dimethyl-7-methoxy-3-phenylchroman.
e. (3R,4R)-2,2-Dimethyl-7-methoxy-4-(4-[{2R}-3-pentylamino-2-hydroxy}propyloxy]phenyl)-3-phenylchroman.
f. (3R,4R)-2,2-Dimethyl-4-(4-[{2R}-3-dimethylamino-2-hydroxy}propyloxy]phenyl)-7-methoxy-3-phenylchroman.
g. (3R,4R)-4-(4-[{2R}-3-Diethylamino-2-hydroxy}propyloxy]phenyl)-2,2-dimethyl-7-methoxy-3-phenylchroman.
h. (3R,4R)-2,2-Dimethyl-4-(4-[{2R}-3-dipropylamino-2-hydroxy}propyloxy]phenyl)-7-methoxy-3-phenylchroman.
i. (3R,4R)-4-(4-[{2R}-3-Dibutylamino-2-hydroxy}propyloxy]phenyl)-2,2-dimethoxy-3-phenylchroman.
j. (3R,4R)-2,2-Dimethyl-4-(4-[{2R}-3-dipentylamino-2-hydroxy}propyloxy]phenyl)-7-methoxy-3-phenylchroman.
k. (3R,4R)-2,2-Dimethyl-7-methoxy-3-phenyl-4-(4-[{2R}-3-pyrrolidino-2-hydroxy}propyloxy]phenyl)-chroman.
l. (3R,4R)-2,2-Dimethyl-7-methoxy-3-phenyl-4-(4-[{2R}-3-piperidino-2-hydroxy}propyloxy]phenyl)-chroman.
m. (3R,4R)-2,2-Dimethyl-7-methoxy-3-phenyl-4-(4-[{2R}-3-morpholino-2-hydroxy}propyloxy]phenyl)-chroman.
n. (3R,4R)-2,2-Dimethyl-7-methoxy-3-phenyl-4-(4-[{2R}-3-piperazino-2-hydroxy}propyloxy]phenyl)-chroman.
o. (3R,4R)-2,2-Dimethyl-7-methoxy-3-phenyl-4-(4-[{2R}-3-cyclohexylamino-2-hydroxy}propyloxy]phenyl)-chroman.
p. (3R,4R)-2,2-Dimethyl-7-methoxy-4-(4-[{2S}-3-methylamino-2-hydroxy}propyloxy]phenyl)-3-phenylchroman.
q. (3R,4R)-2,2-Dimethyl-7-methoxy-4-(4-[{2S}-3-ethylamino-2-hydroxy}propyloxy]phenyl)-3-phenylchroman.
r. (3R,4R)-2,2-Dimethyl-7-methoxy-3-phenyl-4-(4-[{2S}-3-propylamino-2-hydroxy}propyloxy]phenyl)-chroman.
s. (3R,4R)-4-4-(4-[{$^2$S}-3-Butylamino-2-hydroxy}propyloxy]phenyl)-2,2-dimethyl-7-methoxy-3-phenylchroman.
t. (3R,4R)-2,2-Dimethyl-7-methoxy-4-(4-[{2S}-3-pentylamino-2-hydroxy}propyloxy]phenyl)-3-phenylchroman.
u. (3R,4R)-2,2-Dimethyl-4-(4-[{2S}-3-dimethylamino-2-hydroxy}propyloxy]phenyl)-7-methoxy-3-phenylchroman.
v. (3R,4R)-4-(4-[{2S}-3-Diethylamino-2-hydroxy}propyloxy]phenyl)-2,2-dimethyl-7-methoxy-3-phenylchroman.
w. (3R,4R)-2,2-Dimethyl-4-(4-[{2S}-3-dipropylamino-2-hydroxy}propyloxy]phenyl)-7-methoxy-3-phenylchroman.
x. (3R,4R)-4-(4-[{2S}-3-Dibutylamino-2-hydroxy}propyloxy]phenyl)-3-phenyl)-2,2-dimethoxy-3-phenylchroman.
y. (3R,4R)-2,2-Dimethyl-4-(4-[{2S}-3-dipentylamino-2-hydroxy}propyloxy]phenyl)-7-methoxy-3-phenylchroman.
z. (3R,4R)-2,2-Dimethyl-7-methoxy-3-phenyl-4-(4-[{2S}-3-pyrrolidino-2-hydroxy}propyloxy]phenyl)-chroman.
aa. (3R,4R)-2,2-Dimethyl-7-methoxy-3-phenyl-4-(4-[{2S}-3-piperidino-2-hydroxy}propyloxy]phenyl)-chroman.
bb. (3R,4R)-2,2-Dimethyl-7-methoxy-3-phenyl-4-(4-[{2S}-3-morpholino-2-hydroxy}propyloxy]phenyl)-chroman.
cc. (3R,4R)-2,2-Dimethyl-7-methoxy-3-phenyl-4-(4-[{2S}-3-piperazino-2-hydroxy}propyloxy]phenyl)-chroman.
dd. (3R,4R)-2,2-Dimethyl-7-methoxy-3-phenyl-4-(4-[{2S}-3-cyclohexylamino-2-hydroxy}propyloxy]phenyl)-chroman.
ee. (3R,4R)-2,2-Dimethyl-7-methoxy-4-(4-[{3-methylamino-2-hydroxy}propyloxy]phenyl)-3-phenylchroman.
ff. (3R,4R)-2,2-Dimethyl-7-methoxy-4-(4-[{3-ethylamino-2-hydroxy}propyloxy]phenyl)-3-phenylchroman.
gg. (3R,4R)-2,2-Dimethyl-7-methoxy-4-(4-[{3-propylamino-2-hydroxy}propyloxy]phenyl)-3-phenylchroman.
hh. (3R,4R)-4-(4-[{3-butylamino-2-hydroxy}propyloxy]phenyl)-2,2-dimethyl-7-methoxy-3-phenylchroman.
ii. (3R,4R)-2,2-Dimethyl-7-methoxy-4-(4-[{3-pentylamino-2-hydroxy}propyloxy]phenyl)-3-phenylchroman.
jj. (3R,4R)-2,2-Dimethyl-4-(4-[{3-dimethylamino-2-hydroxy}propyloxy]phenyl)-7-methoxy phenyl)-3-phenylchroman.
kk. (3R,4R)-4-(4-[{3-Diethylamino-2-hydroxy}propyloxy]phenyl)-2,2-dimethyl-7-methoxy-3-phenylchroman.
ll. (3R,4R)-2,2-Dimethyl-4-(4-[{3-dipropylamino-2-hydroxy}propyloxy]phenyl-7-methoxy phenyl)-3-phenylchroman.
mm. (3R,4R)-4-(4-[{3-Dibutylamino-2-hydroxy}propyloxy]phenyl)-2,2-dimethoxy-3-phenylchroman.
nn. (3R,4R)-2,2-Dimethyl-4-(4-[{3-dipentylamino-2-hydroxy}propyloxy]phenyl-7-methoxy phenyl)-3-phenylchroman.
oo. (3R,4R)-2,2-Dimethyl-7-methoxy-3-phenyl-4-(4-[{3-pyrrolidino-2-hydroxy}propyloxy]phenyl)-chroman.

pp. (3R,4R)-2,2-Dimethyl-7-methoxy-3-phenyl-4-(4-[{3-piperidino-2-hydroxy}propyloxy]phenyl)-chroman.

qq. (3R,4R)-2,2-Dimethyl-7-methoxy-3-phenyl-4-(4-[{3-morpholino-2-hydroxy}propyloxy]phenyl)-chroman.

rr. (3R,4R)-2,2-Dimethyl-7-methoxy 3-phenyl-4-(4-[{3-piperazino-2-hydroxy}propyloxy]phenyl)-chroman.

ss. (3R,4R)-2,2-Dimethyl-7-methoxy-3-phenyl-4-(4-[{3-cyclohexylamino-2-hydroxy}propyloxy]phenyl)-chroman.

In still another main embodiment of the present invention, wherein the salts are selected from a group comprising acid addition salts consisting of formate, acetate, phenyl acetate, trifluroacetate, acrylate, ascorbate, benzoate, chlorobenzoates, bromobezoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacte, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, toluene sulphonates, and the likes. Additionally, the invention includes alkyl or aryl halides addtion salts of the compounds of this invention, wherein the alkyl halide is selected from a group comprising $C_1$ to $C_{18}$ alkyl halide, and aryl halide is selected from a group comprising benzyl halide and substituted benzyl halide.

In still another main embodiment of the present invention, wherein most preferred salts are fumerate, ascorbate, hydrochloride, and methyl iodide.

In still another main embodiment of the present invention, wherein the compounds or its salts are in the physical forms of the gelatin capsules or compressed into tablets or pills or may be formulated in the form of lozenges, inclusion complexes with cyclodextrin derivatives, injectable depo formulations, aerosols, granules, powders, oral liquids, mucosal adhesive formulations, gel formulations, troches, elixirs, suspensions, syrups, wafers, liposomal delivery systems, implants, suppository, pessary, microemulsions, nanoemulsion, microparticles, nanoparticles, controlled release delivery systems, transdermal delivery systems, and targeted delivery systems such as conjugates with monoclonal antibodies or with other suitable carrier moieties.

In still another main embodiment of the present invention, wherein the pharmaceutically acceptable excipients are selected from a group comprising:

i. diluent such as lactose, mannitol, sorbitol, microcrystalline cellulose, sucrose, sodium citrate, dicalcium phosphate, or any other ingredient of the similar nature alone or in a suitable combination thereof;

ii. a binder such as gum tragacanth, gum acacia, methyl cellulose, gelatin, polyvinyl pyrrolidone, starch or any other ingredient of the similar nature alone or in a suitable combination thereof;

iii. a disintegrating agent such as agar-agar, calcium carbonate, sodium carbonate, silicates, alginic acid, corn starch, potato tapioca starch, primogel or any other ingredient of the similar nature alone or in a suitable combination thereof;

iv. a lubricant such as magnesium stearate, calcium stearate or steorotes, talc, solid polyethylene glycols, sodium lauryl sulphate or any other ingredient of the similar nature alone or in a suitable combination thereof;

v. a glidant such as colloidal silicon dioxide or any other ingredient of the similar nature alone or in a suitable combination thereof;

vi. a sweetening agent such as sucrose, saccharin or any other ingredient of the similar nature alone or in a suitable combination thereof;

vii. a flavoring agent such as peppermint, methyl salicylate, orange flavor, vanilla flavor, or any other pharmaceutically acceptable flavor alone or in a suitable combination thereof;

viii. a wetting agents such as cetyl alcohol, glyceryl monostearate or any other pharmaceutically acceptable flavor alone or in a suitable combination thereof;

xi. a absorbents such as kaolin, bentonite clay or any other pharmaceutically acceptable flavor alone or in a suitable combination thereof; and x. a solution retarding agents such as wax, paraffin or any other pharmaceutically acceptable flavor alone or in a suitable combination thereof.

In another main embodiment of the present invention, wherein a process for the preparation of compounds of formula I, said process comprising steps of:

a. reacting a compound of formula V in which substituents $R^2$ and $R^6$ are arranged in the (3R,4R) configuration: wherein $R^1$ and $R^2$ are as defined in formula 1 and $R^6$ is phenyl substituted with a hydroxy substituents at C2, C3 or C4, preferably at C4 with a compound of formula VI, VII, VIII, neat or in an aprotic solvent which includes dimethylsulphoxide, dimethylformamide in the presence of a base such as $K_2CO_3$ at temperature ranging between 50 to 120° C., b. obtaining compounds of structure IX (a-c) wherein $R^1$ and $R^2$ are as defined in formula 1, (V)

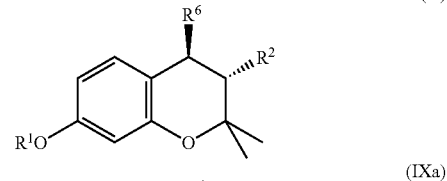

(IXa)

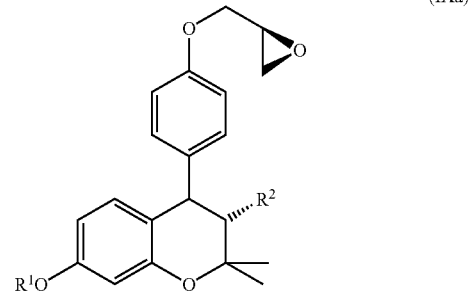

(IXb)

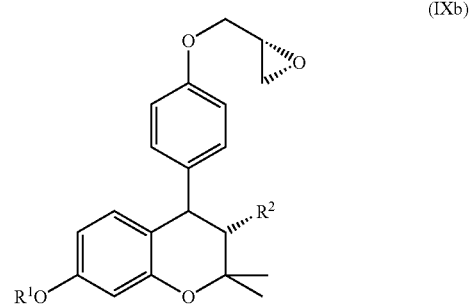

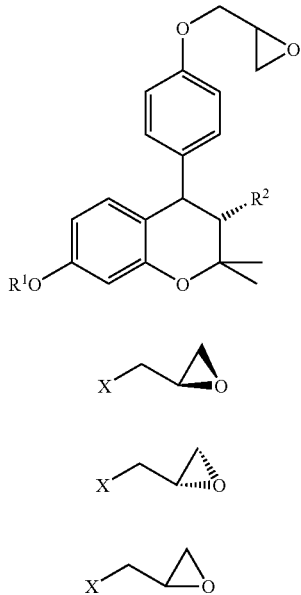

(IXc)

(VI)
R

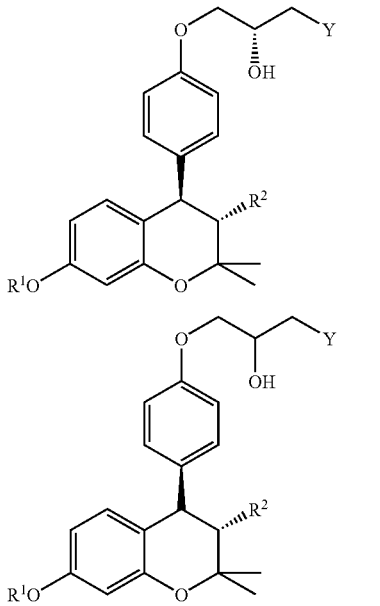

(VII)
S (VIII)
R, S c. reacting compound of formula IX (a-c) with a nucleophile, preferably an amine of formula X, wherein $R^7$ and $R^8$ are individually hydrogen, C1-C6-alkyl which includes straight chain as well as branched alkyl groups such as methyl, ethyl, propyl, isopropyl, butyl, isobutyl C1-C6-cycloalkyl which includes cyclopropane, cyclobutane, cyclopentane, cyclohexane or form a C3-C7 heterocyclic ring, saturated or unsaturated, containing one or two heteroatoms independently selected from the group comprising O, S and N, optionally being substituted with 1, 2, 3 substituents independently selected from the group comprising H, OH, halogen, nitro, cyano, SH, $SR^4$, trihalo-C1-C6-alkyl, C1-C6-alkyl and C1-C6-alkoxy, wherein $R^4$ is defined above, either neat or in the presence of organic solvent such as benzene, dimethylsulphoxide, dimethylformamide, and d. obtaining compounds of formula XI (a-c), optionally converting the amino derivative into their corresponding salts such as HCL, fumarate, citrate by treating the free base with the corresponding acid.

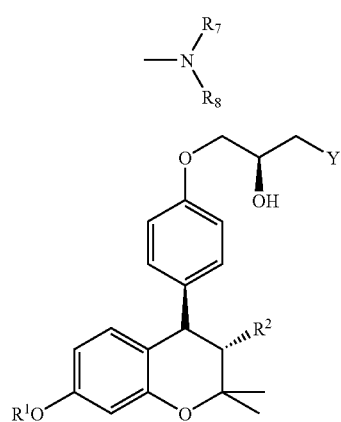

(X)

(XIa)

e. wherein Y, $R^1$ and $R^2$ are as defined above.

In still another main embodiment of the present invention, wherein a method of preventing and/or treating estrogen-related disease conditions in a subject in need thereof, said method comprising step of administering to the subject, a pharmaceutically effective amount of compounds of formula 1, or its salts, optionally along with pharmaceutically acceptable excipients.

In still another main embodiment of the present invention, wherein the salts are selected from a group comprising acid addition salts consisting of formate, acetate, phenyl acetate, trifluroacetate, acrylate, ascorbate, benzoate, chlorobenzoates, bromobezoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacte, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, toluene sulphonates, and the likes. Additionally, the invention includes alkyl or aryl halides addtion salts of the compounds of this invention, wherein the alkyl halide is selected from a group comprising $C_1$ to $C_{18}$ alkyl halide, and aryl halide is selected from a group comprising benzyl halide and substituted benzyl halide.

In still another main embodiment of the present invention, wherein most preferred salts are fumarate, ascorbate, hydrochloride, and methyl iodide.

In still another main embodiment of the present invention, wherein the administration is through various routes selected from a group comprising oral, systemic, local, and topical delivery selected from a group consisting of intravenous, intra-arterial, intra-muscular, subcutaneous, intra-peritoneal, intra-dermal, buccal, intranasal, inhalation, vaginal, rectal, and transdermal.

In still another main embodiment of the present invention, wherein the preferred route of administration is oral route.

In still another main embodiment of the present invention, wherein the physical forms of the compound of formula 1 and its salts could be gelatin capsules or compressed into the tablets or pills or may be formulated in the form of lozenges, inclusion complexes with cyclodextrin derivatives, injectable depo formulations, aerosols, granules, powders, oral liquids, mucosal adhesive formulations, gel formulations, troches, elixirs, suspensions, syrups, wafers, liposomal delivery systems, implants, suppository, pessary, microemulsions, nanoemulsion, microparticles, nanoparticles, controlled release delivery systems, transdermal delivery systems, and targeted delivery systems such as conjugates with monoclonal antibodies or with other suitable carrier moieties.

In still another main embodiment of the present invention, wherein the pharmaceutically acceptable excipients are selected from a group comprising:
i. diluent such as lactose, mannitol, sorbitol, microcrystalline cellulose, sucrose, sodium citrate, dicalcium phosphate, or any other ingredient of the similar nature alone or in a suitable combination thereof;
ii. a binder such as gum tragacanth, gum acacia, methyl cellulose, gelatin, polyvinyl pyrrolidone, starch or any other ingredient of the similar nature alone or in a suitable combination thereof;
iii. a disintegrating agent such as agar-agar, calcium carbonate, sodium carbonate, silicates, alginic acid, corn starch, potato tapioca starch, primogel or any other ingredient of the similar nature alone or in a suitable combination thereof;
iv. a lubricant such as magnesium stearate, calcium stearate or steorotes, talc, solid polyethylene glycols, sodium lauryl sulphate or any other ingredient of the similar nature alone or in a suitable combination thereof;
v. a glidant such as colloidal silicon dioxide or any other ingredient of the similar nature alone or in a suitable combination thereof;
vi. a sweetening agent such as sucrose, saccharin or any other ingredient of the similar nature alone or in a suitable combination thereof;
vii. a flavoring agent such as peppermint, methyl salicylate, orange flavor, vanilla flavor, or any other pharmaceutically acceptable flavor alone or in a suitable combination thereof;
viii. a wetting agent such as cetyl alcohol, glyceryl monostearate or any other pharmaceutically acceptable flavor alone or in a suitable combination thereof;
xi. an absorbent such as kaolin, bentonite clay or any other pharmaceutically acceptable flavor alone or in a suitable combination thereof; and
x. a solution retarding agent such as wax, paraffin or any other pharmaceutically acceptable flavor alone or in a suitable combination thereof.

In still another main embodiment of the present invention, wherein said method helps in preferably diseases or syndromes caused by an estrogen-deficient state, with Relative Binding affinity (RBA) to estrogen receptors ranging between 5 to 7.

In still another main embodiment of the present invention, wherein said method helps in disease conditions caused by osteoporosis, bone loss, and bone formation, with T/C ratio of ≦0.6.

In still another main embodiment of the present invention, wherein said method helps in disease conditions affecting cardiovascular systems, more particularly hyperlipidaemia, thrombosis and vasomotor system.

In still another main embodiment of the present invention, wherein said method helps in disease conditions showing neurodegenerative effects, more particularly, stroke, senile dementia-Alzheimer type and Parkinson disease.

In still another main embodiment of the present invention, wherein said method helps in disease conditions showing menopausal symptoms, more particularly, hot flushes, urogenital atrophy, depression, mania, schizophrenia, urinary incontinence, dysmenorrhea, dysfunctional uterine bleeding, acne, hirsutism, improper ovarian development.

In still another main embodiment of the present invention, wherein said method helps in disease conditions showing cancers, more particularly, prostatic carcinoma, breast cancer, cancer of uterus, cancer of the cervix and colon cancer, with $LC_{50}$ ranging between 17 to 20 μM.

In still another main embodiment of the present invention, wherein the volume of the tumor decreases by about 25%.

In still another main embodiment of the present invention, wherein said method helps regulate fertility in humans and in other animals.

In still another main embodiment of the present invention, wherein said method helps in threatened or habitual abortion.

In still another main embodiment of the present invention, wherein said method helps in suppression of post-partum lactation.

In still another main embodiment of the present invention, wherein said method helps in the management of certain physiological disorders, more particularly, obesity and depression.

In still another main embodiment of the present invention, wherein said method helps regulate of glucose metabolism in non-insulin dependent diabetes mellitus.

In accordance with the principal embodiment, the present invention provides a class of novel (3R, 4R)-trans-3,4-diarylchroman derivatives of the formula (1) or pharmaceutically acceptable salts or pharmaceutically acceptable compositions thereof in which substituents $R^2$ and $R^3$ are arranged in the (3R,4R)-trans-configuration wherein:

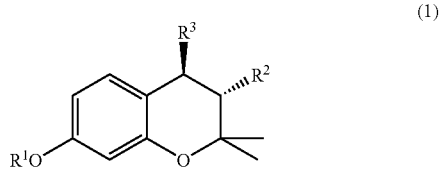

(1)

$R^1$ is H or C1-C6 alkyl;
$R^2$ is phenyl, optionally substituted with 1 to 5 substituents independently selected from the group consisting of OH, C1-C6-alkyl, halogen, nitro, cyano, SH, $SR^4$, trihalo-C1-C6-alkyl, C1-C6-alkoxy and phenyl, wherein $R^4$ is C1-C6 alkyl; C3-C7 cycloalkyl;
$R^3$ is phenyl substituted with O—$R^5$ wherein $R^5$ has the formula (II), (III) or (IV)

(II)

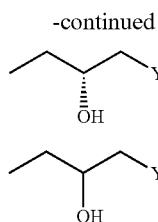

wherein Y is chosen from $NHR^4$, $NR^4_2$, $NHCOR^4$, $NHSO_2R^4$, $CONHR^4$, $CONR^4$, $CONR^4_2$, COOH, $COOR^4$, $SO_2R^4$, $SOR^4$, $SONHR^4$, $SONR^4_2$, a C3-C7 heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-C1-C6-alkyl, C1-C6-alkyl and C1-C6-alkoxy, wherein $R^4$ is as defined above, and pharmaceutically acceptable esters, ethers and salts thereof.

The general chemical terms used in the above formula have their usual meanings. For example, the term C1-C6-alkyl includes straight chain as well as branched alkyl groups such as methyl as ethyl, propyl, isopropyl, butyl and isobutyl.

The term halogen means chloro, bromo, iodo and fluoro.

The term C3-C7-heterocyclic ring include groups such as pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isozazolyl, oxazolyl, oxadiazolyl, thiadiazolyl and thiazolyl.

In an important embodiment, the present invention provides a pharmaceutical composition comprising a therapeutically effective amount of a compound of formula 1 or a pharmaceutically acceptable salt thereof, alone or in a combination of an estrogen or a progestin or both and one or more pharmaceutically acceptable carrier or excipients.

In another embodiment, the present invention provides a medical method of employing the compounds of the present invention or pharmaceutically acceptable salts and compositions thereof and methods of using such compounds for the prevention or treatment of symptoms of estrogen deficiency or deprivation including estrogen deficient or deprivation states in mammals, in particular osteoporosis, bone loss, bone formation, cardiovascular effects more particularly hyperlipidaemia.

In another embodiment of the medical methods of the present invention, the compounds of the present invention or pharmaceutically acceptable salts and compositions thereof are employed in the prevention or the treatment of estrogen dependent cancers such as cancer of breast.

In yet another alternative embodiment of the medical methods of the present invention, the compounds of the present invention are employed in the prevention or the treatment of disease conditions or disorders associated with an aberrant physiological response to endogenous estrogen including regulation of fertility in humans and in other animals.

The present invention relates to the field of pharmaceuticals and organic chemistry and provides new (3R,4R)-trans-3,4-diarylchroman derivatives, their pharmaceutically acceptable salts and compositions that are useful for the prevention or treatment of various medical indications associated with estrogen dependent or independent diseases or syndromes, preferably in prevention or treatment of diseases and syndromes caused by:

(a) estrogen deficient or deprivation state in a mammal, in particular osteoporosis, bone loss, bone formation, cardiovascular effects more particularly hyperlipidaemia, thrombosis and vasomotor system, neurodegenerative effects such as stroke, senile dementia-Alzheimer type and Parkinson disease, menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism;

(b) estrogen dependent or estrogen independent cancers such as prostatic carcinoma, cancer of breast, cancer of uterus, cancer of the cervix and cancer of the colon;

(c) an aid in ovarian development or function;

(d) control or regulation of fertility in humans and in other animals;

(e) prevention of threatened or habitual abortion;

(f) suppression of post-partum lactation;

(g) physiological disorders such as obesity, depression etc.;

(h) regulation of glucose metabolism in non-insulin dependent diabetes mellitus.

The present invention further relates to the processes for the preparation of pharmaceutically active compounds, their pharmaceutically acceptable salts and compositions of the principal aspect of the present invention.

The present invention provides novel (3R,4R)-trans-3,4-diarylchroman derivatives of the formula (1) or pharmaceutically acceptable salts or pharmaceutically acceptable compositions thereof in which substituents $R^2$ and $R^3$ are arranged in the (3R,4R)-trans-configuration wherein:

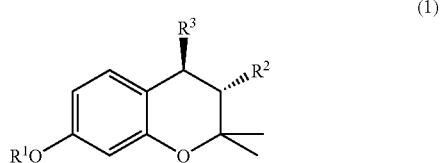

$R^1$ is H or C1-C6 alkyl;
$R^2$ is phenyl, optionally substituted with 1 to 5 substituents independently selected from the group consisting of OH, C1-C6-alkyl, halogen, nitro, cyano, SH, $SR^4$, trihalo-C1-C6-alkyl, C1-C6-alkoxy and phenyl, wherein $R^4$ is C1-C6 alkyl; C3-C7 cycloalkyl;
$R^3$ is phenyl substituted with O—$R^5$ wherein $R^5$ has the formula (II), (III) or (IV)

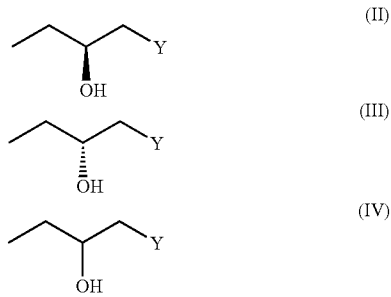

wherein Y is chosen from NHR$^4$, NR$^4_2$, NHCOR$^4$, NHSO$_2$R$^4$, CONHR$^4$, CONR$^4$, CONR$^4_2$, COOH, COOR$^4$, SO$_2$R$^4$, SOR$^4$, SONHR$^4$, SONR$^4_2$, a C3-C7 heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR$^4$, trihalo-C1-C6-alkyl, C1-C6-alkyl and C1-C6-alkoxy, wherein R$^4$ is as defined above, and pharmaceutically acceptable esters, ethers and salts thereof.

The general chemical terms used in the above formula have their usual meanings.

For example the term C1-C6-alkyl includes straight chain as well as branched alkyl groups such as methyl as ethyl, propyl, isopropyl, butyl and isobutyl.

The term halogen means chloro, bromo, iodo and fluoro.

The term C3-C7-heterocyclic ring include groups such as pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl and thiazolyl.

The compounds of this invention or pharmaceutically acceptable salts and compositions thereof are novel Selective Estrogen Receptor Modulators and provide methods of using such compounds for the prevention or treatment of symptoms of estrogen deficiency or deprivation including estrogen deficient or deprivation state in mammals, in particular osteoporosis, bone loss, bone formation, cardiovascular effects more particularly hyperlipidaemia, prevention or the treatment of estrogen dependent or estrogen independent cancers such as cancer of breast and control or regulation of fertility in humans and in other animals.

The term "estrogen deficiency or deprivation" is meant to imply the conditions where the optimal level of estrogen is absent. This level varies from one tissue to another depending on the function of the tissue. Thus, in some cases, estrogen deficiency or deprivation may be total absence of estrogen, whereas in other cases, deficiency or deprivation may involve estrogen levels, which are too low for proper tissue function. In women, the two most common causes of estrogen deprivation are menopause and ovariectomy, although other conditions may be causative.

The term "pharmaceutically acceptable salts" as used through out this specification and the appended claims denotes salts of the types disclosed in the article by Berge et al. (J. Phramaceutical Sciences, 66 (1), 1-19, 1977). Suitable pharmaceutically acceptable salts include salts formed by in-organic acids such as hydrochloric acid, hydrobromic acid, hydroiodic acid, nitric acid, sulphuric acid, phosphoric acid, hypophosphoric acid, and the like, as well as the salts derived from organic acids such as aliphatic mono and dicarboxylic acids, phenyl substituted alkanoic acids, aromatic acids, aliphatic and aromatic sulphonic acids. Also, the salts derived from alkyl halides (preferably, methyl iodide) and aryl halides.

Such pharmaceutically acceptable acid addition salts include formate, acetate, phenyl acetate, trifluroacetate, acrylate, ascorbate, benzoate, chlorobenzoates, bromobezoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacte, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, toluene sulphonates, and the like. Additionally, the invention includes alkyl or aryl halides addtion salts of the compounds of this invention, wherein the alkyl halide is selected from a group comprising $C_1$ to $C_{18}$ alkyl halide, and aryl halide is selected from a group comprising benzyl halide and substituted benzyl halide.

Most preferred salts are fumarate or ascorbate or hydrochloride.

Pharmaceutical compositions of the compound of the present invention or a pharmaceutically acceptable salt thereof may be prepared by procedures known in the art using pharmaceutically acceptable excipients known in the art.

Methods of preventing or treating disorders or disease conditions mentioned herein comprise administering, to an individual human being or any other mammal or any other animal in need of such treatment, a therapeutically effective amount of one or more of the compounds of this invention or a pharmaceutically acceptable salt or a pharmaceutically acceptable composition thereof with one or more of the pharmaceutically acceptable carriers, excipients etc.

The dosage regimen and the mode of administration of the compound of this invention or a pharmaceutically acceptable salt or a pharmaceutically acceptable composition thereof with one or more of the pharmaceutically acceptable carriers, excipients etc. will vary according to the type of disorder or disease conditions described herein and will be subject to the judgment of the medical practitioner involved.

The compound of this invention or a pharmaceutically acceptable salt or a pharmaceutically acceptable composition thereof with one or more of the pharmaceutically acceptable carriers, excipients etc. may be effectively administered in doses ranging from 0.1 mg to 1000 mg, more preferably in doses ranging from 0.5 to 500 or still more preferably in the doses ranging from 1 mg to 100 mg weekly or bi-weekly or daily or twice a day or three times a day or in still more divided doses.

Therapeutically effective amounts of a compound of the present invention or a pharmaceutically acceptable salt thereof may be enclosed in gelatin capsules or compressed into the tablets or pills or may be formulated in the form of lozenges, inclusion complexes with cyclodextrin derivatives, injectable depo formulations, aerosols, granules, powders, oral liquids, mucosal adhesive formulations, gel formulations, troches, elixirs, suspensions, syrups, wafers, liposomal delivery systems, implants, suppository, pessary, microemulsions, nanoemulsion, microparticles, nanoparticles, controlled release delivery systems, transdermal delivery systems, targeted delivery systems such as conjugates with monoclonal antibodies or with other suitable carrier moieties.

Such doses may be administered by any appropriate route for example, oral, systemic, local or topical delivery for example, intravenous, intra-arterial, intra-muscular, subcutaneous, intra-peritoneal, intra-dermal, buccal, intranasal, inhalation, vaginal, rectal, transdermal or any other suitable means in any conventional liquid or solid dosage form to achieve, conventional delivery, controlled delivery or targeted delivery of the compounds of this invention or a pharmaceutically acceptable salt or a pharmaceutically acceptable composition thereof with one or more of the pharmaceutically acceptable carriers, excipients etc.

A preferred mode of administration of a compound of the present invention or a pharmaceutically acceptable salt or a pharmaceutically acceptable composition thereof is oral.

Oral compositions will generally comprise of a compound of the present invention or a pharmaceutically acceptable salt thereof and one or more of the pharmaceutically acceptable excipients.

The oral compositions such as tablets, pills, capsules, powders, granules, and the like may contain any of the following pharmaceutically acceptable excipients:

1. a diluent such as lactose, mannitol, sorbitol, microcrystalline cellulose, sucrose, sodium citrate, dicalcium phosphate, or any other ingredient of the similar nature alone or in a suitable combination thereof;
2. a binder such as gum tragacanth, gum acacia, methyl cellulose, gelatin, polyvinyl pyrrolidone, starch or any other ingredient of the similar nature alone or in a suitable combination thereof;
3. a disintegrating agent such as agar-agar, calcium carbonate, sodium carbonate, silicates, alginic acid, corn starch, potato tapioca starch, primogel or any other ingredient of the similar nature alone or in a suitable combination thereof;
4. a lubricant such as magnesium stearate, calcium stearate or steorotes, talc, solid polyethylene glycols, sodium lauryl sulphate or any other ingredient of the similar nature alone or in a suitable combination thereof;
5. a glidant such as colloidal silicon dioxide or any other ingredient of the similar nature alone or in a suitable combination thereof;
6. a sweetening agent such as sucrose, saccharin or any other ingredient of the similar nature alone or in a suitable combination thereof;
7. a flavoring agent such as peppermint, methyl salicylate, orange flavor, vanilla flavor, or any other pharmaceutically acceptable flavor alone or in a suitable combination thereof;
8. wetting agents such as cetyl alcohol, glyceryl monostearate or any other pharmaceutically acceptable flavor alone or in a suitable combination thereof;
9. absorbents such as kaolin, bentonite clay or any other pharmaceutically acceptable flavor alone or in a suitable combination thereof;
10. solution retarding agents such as wax, paraffin or any other pharmaceutically acceptable flavor alone or in a suitable combination thereof.

In a preferred embodiment, the present invention is concerned with compounds where $R^3$ is phenyl substituted with $OR^5$ wherein $R^5$ has the formula II.

In another preferred embodiment, the present invention is concerned with compounds wherein $R^3$ is phenyl substituted with —$OR^5$ wherein $R^5$ has the formula III and wherein Y is chosen from $NHR^4$, $NR^4_2$, $NHCOR^4$, $NHSO_2R^4$, $CONHR^4$, $CONR^4_2$, COOH, $COOR^4$, $SO_2R^4$, $SOR^4$, $SONHR^4$, or $SONR^4_2$.

In another preferred embodiment, the present invention is concerned with compounds wherein $R^3$ is phenyl substituted with —$OR^5$ wherein $R^5$ has the formula III and wherein Y is a C3-C7 heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-C1-C6-alkyl and C1-C6-alkoxy.

In another preferred embodiment, the present invention is concerned with compounds wherein $R^3$ is phenyl substituted with —$OR^5$ wherein $R^5$ has the formula IV.

In another preferred embodiment, the present invention is concerned with compounds wherein $R^3$ is phenyl substituted with —$OR^5$ wherein $R^5$ has the formula IV and wherein Y is chosen from $NHR^4$, $NR^4_2$, $NHCOR^4$, $NHSO_2R^4$, CONR, $CONR^4_2$, COOH, $COOR^4$, $SO_2R^4$, $SOR^4$, $SONHR^4$, $SONR^4_2$.

In another preferred embodiment, the present invention is concerned with compounds wherein $R^3$ is phenyl substituted with —$OR^5$ wherein $R^5$ has the formula IV and wherein Y is a C3-C7 heterocyclic ring, saturated or containing one or two heteroatoms independently selected from the group consisting of O, S and N, optionally being substituted with 1 to 3 substituents independently selected from the group consisting of H, OH, halogen, nitro, cyano, SH, $SR^4$, trihalo-C1-C6-alkyl and C1-C6-alkoxy.

In another preferred embodiment, the present invention is concerned with compounds in which $OR^1$ is substituted at C5, C6, C7, or C8 position. In another preferred embodiment, the present invention is concerned with compounds in which $OR^1$ is placed at C7 position.

In another preferred embodiment, the present invention is concerned with compounds in which $R^1$ is H, methyl or ethyl, preferably methyl.

In another preferred embodiment, the present invention is concerned with compounds in which $R^2$ is phenyl optionally substituted with 1 to 5 substituents independently selected from the group consisting of OH, C1-C6-alkyl halogen, cyano, trihalo-C1-C6-alkyl and $C_1$-C6-alkoxy, preferably $R^2$ is phenyl.

In another preferred embodiment, the present invention is concerned with compounds in which $R^4$ is methyl, ethyl, propyl, isopropyl, butyl, n-butyl, isobutyl, phenyl, hexyl, preferably butyl.

The compounds of the invention may be prepared by resorting to the chroman chemistry which is well-known in the art, for example in P K Arora, P L Kole and S Ray, Indian J Chem 20 B, 41-5, 1981; S Ray, P K Grover and N Anand, Indian J Chem 9, 727-8, 1971; S Ray, P K Grover, V P Kamboj, B S Setty, A B Kar and N Anand, J Med Chem 19, 276-9, 1976; M Salman, S Ray, A K Agarwal, S Durani, B S Setty, V P Kamboj and N Anand, J Med Chem 26, 592-5, 1983; C Teo, K Sim, Bull Singapore Natl Inst Chem 22, 69-74, 1994; M Salman, P K Arora, S Ray, R C Srimal, Indian J Pharm Sci 49, 43-47, 1987.

However, the invention is further more concerned with a general method of preparation of compounds of formula 1 comprising the steps:

a) reacting a compound of formula V in which substituents $R^2$ and $R^6$ are arranged in the (3R, 4R) configuration: wherein $R^1$ and $R^2$ are as defined in formula 1 and $R^6$ is phenyl substituted with a hydroxy substituent at C2, C3 or C4, preferably at C4 with a compound of formula VI, VII, VIII, neat or in an aprotic solvent which includes dimethylsulphoxide, dimethylformamide in the presence of a base such as $K_2CO_3$ at elevated temperature (50-120° C.) to form a compound of structure IX (a-c) wherein $R^1$ and $R^2$ are as defined above.

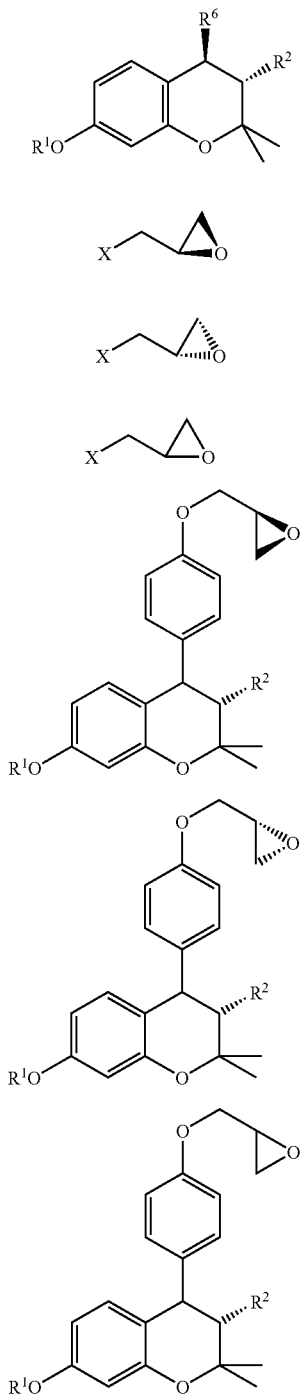
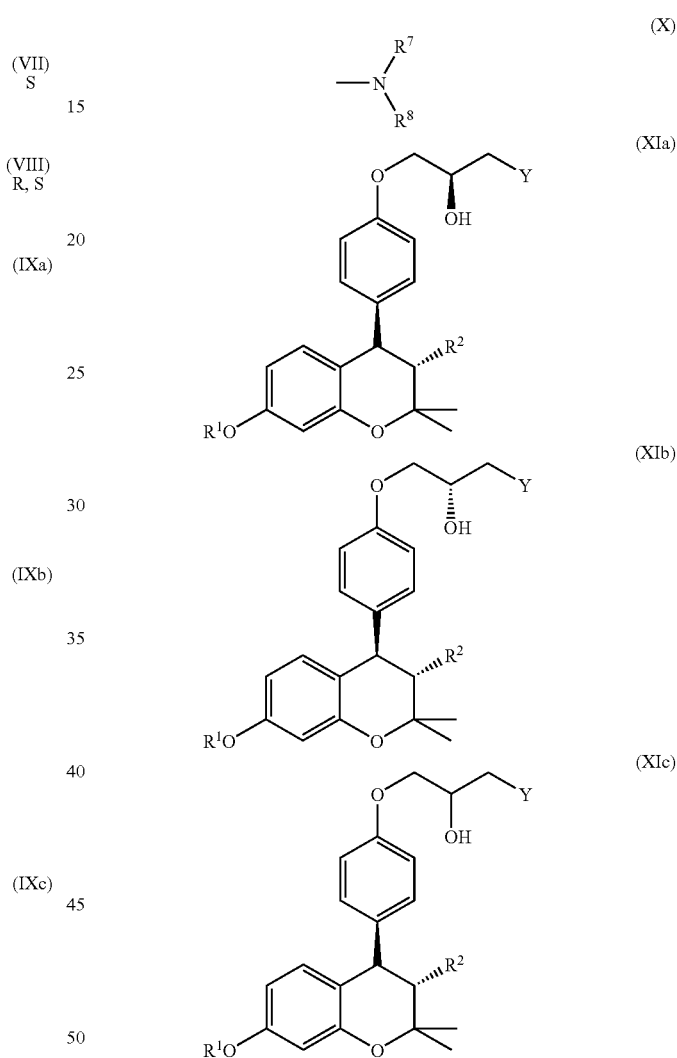

b). reacting compound of formula (IX a-c) with a nucleophile preferably an amine of formula X wherein $R^7$ and $R^8$ are individually hydrogen, C1-C6-alkyl which includes straight chain as well as branched alkyl groups such as methyl, ethyl, propyl, isopropyl, butyl, isobutyl C3-C7-cycloalkyl which includes cyclopropane, cyclobutane, cyclopentane, cyclohexane, cycloheptane or form a C3-C7 heterocyclic ring, saturated or unsaturated, containing one or two heteroatoms independently selected from the group consisting of O, S and N, optionally being substituted with 1,2,3 substituents independently selected from the group consisting of H, OH, halogen, nitro, cyano, SH, $SR^4$, trihalo-C1-C6-alkyl, C1-C6-alkyl and C1-C6-alkoxy, wherein $R^4$ is defined above, either neat or in the presence of organic solvent such as benzene, dimethylsulphoxide, dimethylformamide, to form a compound structure XI (a-c), optionally converting the amino derivative into their corresponding salts such as HCL, fumerate, citrate by treating the free base with the corresponding acid.

wherein Y, $R^1$ and $R^2$ are as defined above.

Further, formula 1 compounds may then be formed as desired. Specific preparations of the compounds of the present invention are described below. Modifications to the above methods may be necessary to accommodate reactive functionalities of particular substituents. Such modification would be both apparent to, and readily ascertained by, those skilled in the art.

Although the free base form of the compounds of the formula 1 can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in the pharmaceutical chemistry. Such salts are also part of this invention. Typical inorganic acids used to form such salts include hydrochloric, hydrobromic, hydroiodic, nitric, sulphuric, phosphoric, hypophosphoric, and the like. Salts derived from the organic acids, such as aliphatic mono and dicarboxylic acids, phenyl substituted alkanoic acids, hydroxyl alkanoic acids, and hydroxyl alkandioic acids, aromatic acids, aliphatic and aromatic sulphonic acids, may also be used. Such pharmaceutically acceptable salts thus include acetate, phenyl acetate, triflurocacetate, acrylate, ascorbate, benzoate, chlorobenzoate, nitrobenzoate, dinitrobenzoate, hydroxylbenzoate, methoxy benzoate, methyl benzoate, acetoxy benzoate, hydrochloride, hydrobromide, hydroiodide, butyrate, phenyl butyrate, hydroxyl butyrate, caprate, caprylate, cinnamate, citrate, formate, succinate, fumarate, glycolate, heptanoate, hippurate, maleate, lactate, malate, hydroxyl maleate, malonate, mandelate, mesylate, nicotinate, isonicotinate, nitrate, oxalate, phthalate, terephthalate, phosphate, monohydrogen phosphate, dihydrogen phosphate, metaphosphate, pyrpphosphate, propioplate, propionate, phenylpropionate, salicylate, sebacate, sulphate, bisulphate, sulphite, bisulphate, sulphonate, benzene sulphonate, p-bromobenzenesulphonate, p-chlorobenzenesulphonate, ethane sulphonate, methane sulphonate, tartarate and the like. Additionally, the invention includes alkyl or aryl halides addtion salts of the compounds of this invention, wherein the alkyl halide is selected from a group comprising $C_1$ to $C_{18}$ alkyl halide, and aryl halide is selected from a group comprising benzyl halide and substituted benzyl halide.

The preferred salts are fumerate, ascorbate, methyl iodide, and hydrochloride salt.

Following examples are presented to further illustrate the preparation of the compounds of the present invention. It is not intended that the invention be limited in scope by reason of any of the following examples:

EXAMPLE 1

3R,4R-trans-2,2-dimethyl-3-phenyl-4-(4-[{2R}-(2,3-epoxy-propyloxy)-phenyl]-7-methoxychroman: (IX a: $R_1$=Me, $R_2$=phenyl)

A mixture of 3R,4R-trans-2,2-dimethyl-3-phenyl-4-[4-hydroxy phenyl]-7-methoxychroman (0.7 g, 1.94 mmol), anhydrous potassium carbonate (2.5 g, 18 mmol), R (−) epichlorohydrin (0.4 ml, 5.11 mmol) in dry DMSO (10 ml) was stirred at 65° C. for 10 hrs. Reaction mixture was poured onto ice-cold water and extracted with ethylacetate, washed with water, dried over anhydrous sodium sulphate and concentrated to give an oil, which was crystallized from benzene-hexane to give the desired product.

Yield: 0.6 g (74.18%), m.p.: 120° C., $[\alpha]_D^{20}$ (C=1, MeOH): −201.96.

IR (KBr, cm$^{-1}$): 1454, 1506, 1585, 1616 (ArH), 1217 (OMe), 2933 (CH), 1382 (gem-dimethyl), 758 (C—O).

$^1$H NMR (δ, CDCl$_3$): 1.2 (s, 3H, gem-dimethyl), 1.3 (s, 3H, gem-dimethyl), 3.1 (d, 1H, monobenzylic H, J=12 Hz), 4.2 (d, 1H, dibenzylic H, J=12 Hz), 6.3-7.3 (m, 12H, ArH), 2.8 (d, 2H,

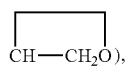

4.0 (d, 2H, OCH$_2$), 3.3 (m, 1H,

Analysis: (C$_{27}$H$_{28}$O$_4$) Calculated (Cald): C, 77.88%; H, 6.73%. Observed (Obsd): C, 77.85%; H, 6.75%. Mass: m/z 416.

EXAMPLE 2

3R,4R-trans-2,2-dimethyl-3-phenyl-4-(4-[{2R}-(3-n-butylamino-2-hydroxy}propyloxy]-phenyl)-7-methoxychroman (HCl salt): (XI a: $R_1$=Me, $R_2$=phenyl, Y=butylamine)

A mixture of 3R,4R-trans-2,2-dimethyl-3-phenyl-4-(4-[{2R}-(2,3-epoxy-propyloxy)-phenyl]-7-methoxychroman (0.2 g, 0.48 mmol), n-butylamine (0.5 ml, 5.06 mmol) and ethanol (15 ml) was refluxed for 3 hrs. Ethanol was distilled off. The obtained residue was purified by passing through basic alumina column using hexane-benzene as eluant. The free base thus obtained was converted into its hydrochloride by treating with ethanolic HCl and crystallized from anhydrous ethanol-diethylether to give the desired product.

Yield: 0.160 g, (63.33%) m.p.: 193° C. $[\alpha]_D^{20}$ (C=1, MeOH): −160.

IR (KBr, cm$^{-1}$): 1506, 1585, 1614 (ArH), 1215 (OMe), 2935 (CH), 3417 (OH), 3719 (amine) 1380 (gem-dimethyl).

$^1$H NMR (δ, CDCl$_3$): 1.2 (s, 3H, gem-dimethyl), 1.3 (s, 3H, gem-dimethyl), 3.1 (d, 1H, monobenzylic H, J=12 Hz), 4.2 (d, 1H, dibenzylic H, J=12 Hz), 3.76 (s, 3H, OMe), 3.83 (d, 2H, OCH$_2$), 4.0 (m, 1H, CHOH), 2.77 (d, 2H, CH$_2$N), 0.87-0.94 (t, 3H, NCH$_2$), 1.20-1.27 (q, 3H, CH$_2$CH$_3$), 2.59-2.71 (m, 4H, 2×(CH$_2$)$_2$).

Analysis: (C$_{31}$H$_{39}$O$_4$N) Cald: C, 76.07%; H, 7.98%; N, 2.86%. Obsd: C, 76.02%; H, 7.95%; N, 2.88%. Mass: m/z 489 [M$^+$-37].

This compound showed promising antiresorptive activity in vitro using chick fetal bone assay with T/C ratio of 0.4 to 0.7 at 25-100 μM concentration in repeat tests, in comparison to Raloxifene having T/C of 0.6. It also prevents pregnancy in rats when administered during the pre-implantation period and has an MED of 0.05 mg/kg dose and is devoid of any estrogenic activity at the MED.

EXAMPLE 3

3R, 4R-trans-2,2-dimethyl-3-phenyl-4-(4-[{2R}-(3-n-butylamino-2-hydroxy}propyloxy]-phenyl)-7-methoxychroman (Citric Acid Salt): (XI a: $R_1$=Me, $R_2$=phenyl, Y=butylamine)

A mixture of 3R,4R-trans-2,2-dimethyl-3-phenyl-4-(4-[{2R}-(2,3-epoxy-propyloxy)-phenyl]-7-methoxychroman (0.2 g, 0.48 mmol), n-butylamine (0.5 ml, 5.06 mmol) and ethanol (15 ml) was refluxed for 3 hrs. Ethanol was distilled off. The obtained residue was purified by passing through basic alumina column using hexane-benzene as eluant. The free base thus obtained was converted into its citrate and crystallized from anhydrous ethanol-diethylether to give the desired product.

Yield: 0.165 g, (63.5%) m.p.: 142° C. $[\alpha]_D^{20}$ (C=1, MeOH): −136.

IR (KBr, cm$^{-1}$): 1437, 1506, 1589, 1614 (ArH), 1240 (OMe), 2966 (CH), 3429 (OH), 3758 (amine) 1380 (gem-dimethyl).

$^1$H NMR (δ, CDCl$_3$): 1.2 (s, 3H, gem-dimethyl), 1.3 (s, 3H, gem-dimethyl), 3.1 (d, 1H, monobenzylic H, J=12 Hz), 4.2 (d, 1H, dibenzylic H, J=12 Hz), 3.72 (s, 3H, OMe), 3.89-3.93 (d, 2H, OCH$_2$), 4.18 (m, 1H, CHOH), 2.77 (d, 2H, CH$_2$N), 0.79-0.82 (t, 3H, NCH$_2$), 1.22-1.35 (q, 3H, CH$_2$CH$_3$), 2.62-2.85 (m, 4H, 2×(CH$_2$)$_2$). Mass: m/z 489 [M$^+$–192].

EXAMPLE 4

3R,4R-Trans-2,2-dimethyl-3-phenyl-4-(4-[{2R)-3-pyrrolidino-2-hydroxy}propyloxy]phenyl)-7-methoxychroman (HCl Salt): (XI a: R$_1$=Me, R$_2$=phenyl, Y=pyrrolidine)

A mixture of 3R,4R-trans-2,2-dimethyl-3-phenyl-4-(4-[{2R)-(2,3-epoxy-propyloxy)-phenyl]-7-methoxychroman (0.2 g, 0.48 mmol), pyrrolidine (0.5 ml, 5.99 mmol) in absolute alcohol (15 ml) was refluxed for 3 hrs. Ethanol was distilled off and the residue purified by passing through basic alumina column using hexane-benzene as eluent. The free base thus obtained was converted into its hydrochloride by treating with ethanolic HCl and crystallized from anhydrous ethanol-diethylether to give the desired product.

Yield: 0.136 g (54.04%), m.p.: 135° C., [α]$_D^{20}$ (C=1, MeOH): –167.64.

IR (KBr, cm$^{-1}$): 1508, 1585, 1610 (ArH), 1245 (OMe), 2927 (CH), 3415 (OH), 3715 (amine) 1370 (gem-dimethyl).

$^1$H NMR (δ, CDCl$_3$): 6.3-7.2 (m, 12H, ArH), 3.1 (d, 1H, monobenzylic H, J=12 Hz), 4.2 (d, 1H, dibenzylic H, J=12 Hz), 1.2 (s, 3H, gem-dimethyl), 1.3 (s, 3H, gem-dimethyl), 3.76 (s, 3H, MeO), 1.7-1.8 (m, 4H, 2×CH$_2$ of pyrrolidine), 2.41-2.49 (m, 4H, 2×NCH$_2$), 3.96 (m, 1H, CHOH), 3.8 (d, 2H, OCH$_2$), 2.75 (d, 2H, CH$_2$N).

Analysis: (C$_{31}$H$_{37}$O$_4$N), Cald: C, 76.39%; H, 7.59%; N, 2.87%. Obsd: C, 76.42%; H, 7.57%; N, 2.83%. Mass: m/z 487 [M$^+$–37].

EXAMPLE 5

3R,4R-Trans-2,2-dimethyl-3-phenyl-4-(4-[{2R)-3-piperidino-2-hydroxy}propyloxy]phenyl)-7-methoxychroman (HCl Salt): (XI a: R$_1$=Me, R$_2$=phenyl, Y=piperidine)

A mixture of 3R,4R-trans-2,2-dimethyl-3-phenyl-4-(4-[{2R)-(2,3-epoxy-propyloxy)-phenyl]-7-methoxychroman (0.160 g, 0.38 mmol), piperidine (0.28 ml, 2.8 mmol) in absolute alcohol (15 ml) was refluxed for 4 hrs. Ethanol was distilled off and the residue purified by passing through basic alumina column using hexane-benzene as eluent. The free base thus obtained was converted into its hydrochloride by treating with ethanolic HCl and crystallized from anhydrous ethanol-diethylether to give the desired product.

Yield: 0.140 g (67.72%), m.p.: 130° C., [α]$_D^{20}$ (C=1, MeOH): –101.50.

IR (KBr, cm$^{-1}$): 1444, 1506, 1584, 1616 (ArH), 1217 (OMe), 2935 (CH), 3396 (OH), 3677 (amine), 1384 (gem-dimethyl).

$^1$H NMR (δ, CDCl$_3$): 1.2 (s, 3H, gem-dimethyl), 1.3 (s, 3H, gem-dimethyl), 3.76 (s, 3H, MeO), 3.1 (d, 1H, monobenzylic H, J=12 Hz), 4.2 (d, 1H, dibenzylic H, J=12 Hz), 3.87 (d, 2H, OCH$_2$), 3.9 (m, 1H, CHOH), 2.7 (d, 2H, CH$_2$N) 6.3-7.2 (m, 12H, ArH), 1.5-1.67 (m, 6H, 3×CH$_2$ piperidine ring), 2.5-2.6 (m, 4H, 2×NCH$_2$).

Analysis: (C$_{32}$H$_{39}$O$_4$N), Cald: C, 76.65%; H, 7.78%; N, 2.79%. Obsd: C, 76.62%; H, 7.77%; N, 2.83%. Mass: m/z 501 [M$^+$–37].

EXAMPLE 6

3R,4R-trans-2,2-dimethyl-3-phenyl-4-(4-[{2S)-(2,3-epoxy-propyloxy)-phenyl]-7-methoxychroman: (IX b: R$_1$=Me, R$_2$=phenyl)

A mixture of 3R,4R-trans-2,2-dimethyl-3-phenyl-4-[4-hydroxy phenyl]-7-methoxychroman (0.7 g, 1.94 mmol), anhydrous potassium carbonate (2.5 g, 18.0 mmol), S (+) epichlorohydrin (0.4 ml, 5.11 mmol) in dry DMSO (10 ml) was stirred at 70° C. for 10 hrs. Reaction mixture was poured onto ice-cold water and extracted with ethylacetate, washed with water, dried over anhydrous sodium sulphate and concentrated to give an oil, which was crystallized from benzene-hexane to give the desired product.

Yield: 0.7 g (86.53%), m.p.: 118° C., [α]$_D^{20}$ (C=1, MeOH): –266.04.

IR (KBr, cm$^{-1}$): 1454, 1506, 1583, 1616 (ArH), 1217 (OMe), 2931(CH), 1382 (gem-dimethyl), 759 (C—O).

$^1$H NMR (δ, CDCl$_3$): 1.2 (s, 3H, gem-dimethyl), 1.3 (s, 3H, gem-dimethyl), 3.1 (d, 1H, monobenzylic H, J=12 Hz), 4.2 (d, 1H, dibenzylic H, J=12 Hz), 6.3-7.2 (m, 12H, ArH), 2.8 (d, 2H,

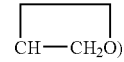

4.0 (d, 2H, OCH$_2$), 3.4 (m, 1H,

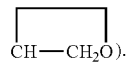).

Analysis: (C$_{27}$H$_{28}$O$_4$), Cald: C, 77.88%; H, 6.73%. Obsd: C, 77.85%; H, 6.72%. Mass: m/z 416.

EXAMPLE 7

3R,4R-trans-2,2-dimethyl-3-phenyl-4-(4-{2S)-3-n-butylamino-2-hydroxy}propyloxy]-phenyl)-7-methoxychroman (HCl Salt): (XI b: R$_1$=Me, R$_2$=phenyl, Y=butylamine)

A mixture of 3R,4R-trans-2,2-dimethyl-3-phenyl-4-(4-[{2S)-(2,3-epoxy-propyloxy)-phenyl]-7-methoxychroman (0.2 g, 0.48 mmol), n-butylamine (0.4 ml, 4.04 mmol) in absolute alcohol (15 ml) was refluxed for 3 hrs. Ethanol was distilled off and the residue obtained was purified by passing through basic alumina column using hexane-benzene as eluent. The free base thus obtained was converted into its hydrochloride by treating with ethanolic HCl and crystallized from anhydrous ethanol-diethylether to give the desired product.

Yield: 0.130 g, (51.46%) m.p.: 140° C., [α]$_D^{20}$ (C=1, MeOH): –151.49.

IR (KBr, cm$^{-1}$): 1465, 1494, 1593, 1614 (ArH), 1215 (OMe), 2943 (CH), 3398 (OH), 3683 (amine), 1340 (gem-dimethyl).

$^1$H NMR (δ, CDCl$_3$): 1.2 (s, 3H, gem-dimethyl), 1.3 (s, 3H, gem-dimethyl), 3.1 (d, 1H, monobenzylic H, J=12 Hz), 4.2 (d, 1H, dibenzylic H, J=12 Hz), 3.76 (s, 3H, OMe), 3.8 (d, 2H, OCH$_2$), 3.96 (m, 1H, CHOH), 0.86-0.94 (t, 3H, CH$_2$CH$_3$), 1.3 (q, 2H, NCH$_2$), 2.58-2.74 (m, 4H, 2×(CH$_2$)$_2$), 2.76 (d, 2H, CH$_2$N).

Analysis: (C$_{31}$H$_{39}$O$_4$N), Cald: C, 76.07%; H, 7.98%; N, 2.86%. Obsd: C, 76.10%; H, 7.98%; N, 2.85%. Mass: m/z 489 [M$^+$–37].

EXAMPLE 8

3R,4R-Trans-2,2-dimethyl-3-phenyl-4-(4-[{2S)-3-pyrrolidino-2-hydroxy}propyloxy]phenyl)-7-methoxychroman (HCl Salt): (XI b: R$_1$=Me, R$_2$=phenyl, Y=pyrrolidine)

A mixture of 3R,4R-trans-2,2-dimethyl-3-phenyl-4-(4-[{2S)-(2,3-epoxy-propyloxy)-phenyl]-7-methoxychroman (0.2 g, 0.48 mmol), pyrrolidine (0.4 ml, 4.79 mmol) in absolute alcohol (15 ml) was refluxed for 3 hrs. Ethanol was distilled off and the residue thus obtained was purified by passing through basic alumina column using hexane-benzene as eluent. The free base thus obtained was converted into its hydrochloride by treating with ethanolic HCl and crystallized from anhydrous ethanol and diethylether to give the desired product.

Yield: 0.210 g (83.44%), m.p.: 140° C., [α]$_D^{20}$ (C=1, MeOH): −133.94 IR (KBr, cm$^{-1}$): 1458, 1506, 1614 (ArH), 1217 (OMe), 2927 (CH), 3408 (OH), 3681 (amine), 1380 (gem-dimethyl).

$^1$H NMR (δ, CDCl$_3$): 6.26-7.18 (m, 12H, ArH), 3.1 (d, 1H, monobenzylic H, J=12 Hz), 4.2 (d, 1H, dibenzylic H, J=12 Hz), 1.2 (s, 3H, gem-dimethyl), 1.3 (s, 3H, gem-dimethyl), 3.69 (s, 3H, MeO), 1.5-1.9 (m, 4H, 2×CH$_2$ pyrrolidine), 2.2-2.3 (m, 4H, 2×NCH$_2$), 4.0 (m, 1H, CHOH), 3.7 (d, 2H, OCH$_2$), 2.75 (d, 2H, CH$_2$N).

Analysis: (C$_{31}$H$_{37}$O$_4$N), Cald: C, 76.39%; H, 7.59%; N, 2.87%. Obsd: C, 76.33%; H, 7.56%; N, 2.85%. Mass: m/z 487 [M$^+$–37].

EXAMPLE 9

3R,4R-Trans-2,2-dimethyl-3-phenyl-4-(4-[{2S)-3-piperidino-2-hydroxy}propyloxy]phenyl)-7-methoxychroman (HCl Salt): (XI b: R$_1$=Me, R$_2$=phenyl, Y=piperidine)

A mixture of 3R,4R-trans-2,2-dimethyl-3-phenyl-4-(4-[{2S)-(2,3-epoxy-propyloxy)-phenyl]-7-methoxychroman (0.2 g, 0.48 mmol), piperidine (0.4 ml, 4.04 mmol) in absolute alcohol (15 ml) was refluxed for 4 hrs. Ethanol was distilled off and the residue thus obtained was purified by passing through basic alumina column using hexane-benzene as eluent. The free base thus obtained was converted into its hydrochloride by treating with ethanolic HCl and crystallized from anhydrous ethanol-dry ether to give the desired product.

Yield: 0.140 g (54.18%), m.p.: 168° C., [α]$_D^{20}$ (C=1, MeOH): −148.84.

IR (KBr, cm$^{-1}$): 1444, 1506, 1584, 1616 (ArH), 1217 (OMe), 2935 (CH), 3396 (OH), 3677 (amine), 1384 (gem-dimethyl).

$^1$H NMR (δ, CDCl$_3$): 1.2 (s, 3H, gem-dimethyl), 1.3 (s, 3H, gem-dimethyl), 3.76 (s, 3H, MeO), 3.1 (d, 1H, monobenzylic H, J=12 Hz), 4.2 (d, 1H, dibenzylic H, J=12 Hz), 3.87 (d, 2H, OCH$_2$), 3.9 (m, 1H, CHOH), 2.7 (d, 2H, CH$_2$N) 6.3-7.2 (m, 12H, ArH), 1.5-1.67 (m, 6H, 3×CH$_2$ piperidine ring), 2.5-2.6 (m, 4H, 2×NCH$_2$).

Analysis: (C$_{32}$H$_{39}$O$_4$N), Cald: C, 76.65%; H, 7.78%; N, 2.79%. Obsd: C, 76.58%; H, 7.74%; N, 2.84%. Mass: m/z 501 [M$^+$–37].

EXAMPLE 10

3R,4R-Trans-2,2-dimethyl-3-phenyl-4-(4-(2,3-epoxypropyloxy)-phenyl)-7-methoxychroman: (IX c: R$_1$=Me, R$_2$=phenyl)

A mixture of 3R,4R-trans-2,2-dimethyl-3-phenyl-4-(4-hydroxy phenyl)-7-methoxy chroman (0.5 g, 1.39 mmol), potassium carbonate (2 g, 14.4 mmol) in racemic epichlorohydrin (10 ml, 127.8 mmol) was refluxed for 12 hrs. at 120° C. Potassium carbonate was filtered off. Reaction mixture was extracted with ethyl acetate, washed with water, dried over anhydrous sodium sulphate and concentrated to give an oil, which was crystallized from methanol to give the desired product.

Yield: 0.454 g (78.58%), m.p.: 113-115° C., [α]$_D^{20}$ (C=1, MeOH): −159.78.

IR (KBr, cm$^{-1}$): 1431, 1506, 1575, 1614 (ArH), 1217 (OMe), 2927 (CH), 1379 (gem-dimethyl), 767(C—O).

$^1$H NMR (δ, CDCl$_3$): 1.2 (s, 3H, gem-dimethyl), 1.3 (s, 3H, gem-dimethyl), 3.3 (d, 1H, monobenzylic H, J=12 Hz), 4.6 (d, 1H, dibenzylic H, J=12 Hz), 6.4-7.3 (m, 12H, ArH), 3.77 (s, 3H, OMe), 2.8 (d, 2H,

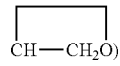

4.10 (d, 2H, OCH$_2$), 3.1 (m, 1H,

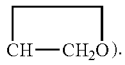

Analysis: (C$_{27}$H$_{28}$O$_4$), Cald: C, 77.88%; H, 6.73%. Obsd: C, 77.86%; H, 6.72%. Mass: m/z 416.

EXAMPLE 11

3R,4R-Trans-2,2-dimethyl-3-phenyl-4-(4-(2-hydroxy-3n-butylaminopropyloxy)-phenyl)-7-methoxychroman (HCl Salt): (XI c: R$_1$=Me, R$_2$=phenyl, Y=butylamine)

A mixture of 3R,4R-trans-2,2-dimethyl-3-phenyl-4-[4-(2,3 epoxypropyloxy)-phenyl]-7-methoxychroman (0.3 g, 0.72 mmol), n-butylamine (0.4 ml, 4.05 mmol) and absolute alcohol (10 ml) was refluxed for 3 hrs. Ethanol was distilled off and residue purified by passing through basic alumina column using hexane-benzene as eluent. The free base thus obtained was converted into its hydrochloride by treating with ethanolic HCl and crystallized from anhydrous ethanol-diethylether to give the desired product.

Yield: 0.14 g (36.94%), m.p.: 210° C., [α]$_D^{20}$ (C=1, MeOH): −170.23.

IR (KBr, cm$^{-1}$): 1458, 1508, 1550, 1614 (ArH), 1232 (OMe), 2935 (CH), 3246 (OH), 3411 (amine), 1358 (gem-dimethyl).

$^1$H NMR (δ, CDCl$_3$): 1.2 (s, 3H, gem-dimethyl), 1.3 (s, 3H, gem-dimethyl), 3.1 (d, 1H, monobenzylic H, J=12 Hz), 4.2

(d, 1H, dibenzylic H, J=12 Hz), 3.77 (s, 3H, OMe), 1.4-2.3 (m, 9H, NCH$_2$C3H$_7$), 2.7 (d, 2H, NCH$_2$), 3.98 (d, 2H, OCH$_2$), 4.0 (m, 1H, CHOH).

Analysis: (C$_{31}$H$_{39}$O$_4$N) Cald: C, 76.07%; H, 7.98%; N, 2.86%. Obsd: C, 76.1%; H, 6.97%; N, 2.83%. Mass: m/z 489 [M$^+$–37].

EXAMPLE 12

3R,4R-Trans-2,2-dimethyl-3-phenyl-4-(4-(2-hydroxy-3-pyrrolidinopropyloxy)-phenyl)-7-methoxy chroman (HCl Salt): (XI c: R$_1$=Me, R$_2$=phenyl, Y=pyrrolidine)

A mixture of 3R,4R-trans-2,2-dimethyl-3-phenyl-4-(4(2,3 epoxypropyloxy)-phenyl)-7-methoxychroman (0.9 g, 2.16 mmol), pyrrolidine (5 ml, 5.99 mmol) in absolute alcohol (15 ml) was refluxed for 4 hrs. Ethanol was distilled off and passing through basic alumina column using benzene-hexane as eluent purified the residue thus obtained. The free base thus obtained was converted into its hydrochloride by treating with ethanolic HCl and crystallized from dry ethanol-diethylether to give the desired compound.

Yield: 0.9 g (79.46%), m.p.: 180° C., $[\alpha]_D^{20}$ (C=1, MeOH): –174.25.

IR (KBr, cm$^{-1}$): 1456, 1506, 1556, 1612 (ArH), 1232 (OMe), 2945 (CH), 3258 (OH), 3506 (amine), 1370 (gem-dimethyl).

$^1$H NMR (δ, CDCl$_3$): 6.3-7.2 (m, 12H, ArH), 3.1 (d, 1H, monobenzylic H, J=12 Hz), 4.2 (d, 1H, dibenzylic H, J=12 Hz), 1.2 (s, 3H, gem-dimethyl), 1.3 (s, 3H, gem-dimethyl), 3.76 (s, 3H, MeO), 1.7-1.8 (m, 4H, 2×CH$_2$ of pyrrolidine), 2.41-2.49 (m, 4H, 2×NCH$_2$), 3.96 (m, 1H, CHOH), 3.8 (d, 2H, OCH$_2$), 2.75 (d, 2H, CH$_2$N).

Analysis: (C$_{31}$H$_{37}$O$_4$N), Cald: C, 76.39%; H, 7.59%; N, 2.87%. Obsd: C, 76.42%; H, 7.57%; N, 2.83%. Mass: m/z 487 [M$^+$–37].

EXAMPLE 13

3R,4R-Trans-2,2-dimethyl-3-phenyl-4-(4-(2-hydroxy-3-piperidinopropyloxy)-phenyl)-7-methoxy-chroman (HCl Salt): (XI c: R$_1$=Me, R$_2$=phenyl, Y=piperidine)

A mixture of 3R,4R-trans-2,2-dimethyl-3-phenyl-4-[4-(2,3-epoxypropyloxy)-phenyl]-7-methoxychroman (0.2 g, 0.48 mmol), piperidine (0.4 ml, 4.04 mmol) and absolute alcohol (10 ml) was refluxed for 4 hrs. Ethanol was distilled off and residue purified by passing through basic alumina column using hexane-benzene as eluant. The free base thus obtained was converted into its hydrochloride by treating with ethanolic HCl and crystallized from anhydrous ethanol-diethyl-ether to give the desired product.

Yield: 0.25 g (96.74%), m.p.: 125-130° C., $[\alpha]_D^{20}$ (C=1, MeOH): –143.14

IR (KBr, cm$^{-1}$): 1444, 1505, 1584, 1615 (ArH), 1242 (OMe), 1383 (gem-dimethyl), 2934 (CH), 3403 (OH), 3647, 3785(amine).

$^1$H NMR (δ, CDCl$_3$): 1.2 (s, 3H, gem-dimethyl), 1.3 (s, 3H, gem-dimethyl), 3.76 (s, 3H, MeO), 3.1 (d, 1H, monobenzylic H, J=12 Hz), 4.2 (d, 1H, dibenzylic H, J=12 Hz), 3.87 (d, 2H, OCH$_2$), 3.9 (m, 1H, CHOH), 2.7 (d, 2H, CH$_2$N) 6.3-7.2 (m, 12H, ArH), 1.5-1.67 (m, 6H, 3×CH$_2$ of piperidine ring), 2.5-2.6 (m, 4H, 2×NCH$_2$).

Analysis: (C$_{32}$H$_{39}$O$_4$N), Cald: C, 76.65%; H, 7.78%; N, 2.79%. Obsd: C, 76.61%; H, 7.77%; N, 2.81%. Mass: m/z 501 [M$^+$–37].

Biological Evaluation

The compounds of the present invention were evaluated for use for the prevention or treatment of symptoms of estrogen deficiency or deprivation including estrogen deficient or deprivation state in mammals, in particular osteoporosis, bone loss, bone formation, cardiovascular effects more particularly hyperlipidaemia, prevention or the treatment of estrogen dependent or estrogen independent cancers such as cancer of breast and control or regulation of fertility in humans and in other animals. Detailed procedures for the evaluation of the compounds of the present invention or pharmaceutically acceptable salts or compositions thereof are described hereunder:

Test Procedure for Evaluation of Antiosteoporosis (Antiresorptive) Activity In Vitro Test solutions of the compounds of the present invention are prepared in appropriate solvents in concentration range of 5 millimolar to 400 millimolar, most preferably in concentrations of 20 millimolar. 5 µl of each concentration are used for evaluation of antiresorptive activity in vitro. In control experiments, 5 µl of appropriate solvent is used in lieu of test compound. Femur bones are isolated from chick embryos on day 11 post-ovulation. The adhering soft connective tissue is completely removed. Each femur bone is then placed in a drop of phosphate buffered saline (PBS) and is transferred to BGJ$_b$ culture medium containing $^{45}$CaCl$_2$ and incubated for 2 h. Labeled femur bones are washed 2-3 times with PBS and transferred to BGJ$_b$ medium containing parathyroid hormone and cultured for 96 h in the presence or absence of the compound of invention or the vehicle in BGJ$_b$ medium. Contralateral femur of each fetus serves as corresponding control. Culture medium with the respective treatment in each well is changed after 48 h. On termination of the culture at 96 h, bones are transferred to 0.1 N HCl for 24 h. Radioactivity due to $^{45}$Ca in the spent medium collected at 48 and 96 h of culture and HCl extract at 96 h of culture is quantified by Liquid Scintillation Spectrophotometer in 10 ml of the scintillation fluid. Bone resorbing activity is expressed as percentage of $^{45}$Ca released into the culture medium and the effect of the compound of invention as percent of the corresponding contra-lateral control or T/C ratio as shown below:

$$T/C \text{ ratio} = \frac{^{45}\text{Ca resorption in presence of } PTH + \text{test agent}}{^{45}\text{Ca resorption in presence of } PTH + \text{vehicle}}$$

Appropriate solvents are selected from solvents like water, normal (physiological) saline, phosphate buffered saline, phosphate buffer, DMSO alone or in a suitable combinations thereof.

In accordance with the above test procedure, the compounds of the present invention, on employing or administering their effective amounts, exhibit positive response by inhibiting the PTH induced resorption of $^{45}$Ca from chick fetal bones in culture. The compounds showing T/C ratio of 0.6 at 100 micromolar (µM) concentration are considered active (Table 1). Activity in the above test procedure indicates that the compounds of the present invention are useful as antiresorptive agents in the treatment of post-menopausal osteoporosis.

TABLE 1

Inhibition in PTH-induced resorption of $^{45}$Ca from chick fetal bones in culture

| Compound | Concentration in µM | T/C ratio |
| --- | --- | --- |
| Example number 1 | 100 | 0.59 |
| Example number 7 | 100 | 0.41 |
| Example number 10 | 100 | 0.79 |
| Example number 12 | 100 | 0.77 |

Test Procedure for Evaluation of Antiosteoporosis Activity In Vivo

The in vivo antiosteoporosis activity is evaluated in colony-bred adult (3-4 month old) female Sprague-Dawley rats or female retired breeder Sprague-Dawley rats (12-14 months old; parity ≧3). Animals are bilaterally ovariectomized (OVX) under light ether anesthesia and treated with the compound of the present invention, 17-alfa-ethynylestradiol (EE) or the vehicle once daily on days 1-30 post-ovariectomy (day 1: day of bilateral ovariectomy) by the oral route. One group of females is sham operated and treated similarly with the vehicle. Animals of all the groups are autopsied 24 h after the last treatment. Before autopsy, 24 h fasting urine samples are collected in fresh containers using all-glass metabolic cages and stored at −20° C. until analyzed for calcium, phosphorus and creatinine. At autopsy, about 5 ml blood samples are collected by cardiac puncture from each rat under light ether anesthesia and serum is isolated and stored at −20° C. until analyzed for total and bone specific alkaline phosphatase, osteocalcin and calcium.

Uterus of each rat is carefully excised, gently blotted, weighed and fixed for histology. Representative sections (5 µm) from each uterus are stained with haematoxylin and eosin. Femur and tibia of each rat are then dissected free of adhering tissue, fixed in 70% ethanol in physiological saline and stored at −20° C. until Bone Mineral Density (BMD) measurement. Before autopsy, whole body scan of each rat for measurement of BMD is performed on an Hologic QDR-4500A fan-beam densitometer, calibrated daily with Hologic hydroxyapatite anthropomorphic spine phantom using manufacturer provided software for small animals. BMD measurement of isolated bones is performed using identical regions of interest. Serum total alkaline phosphatase, osteocalcin, calcium ion content and urinary calcium and creatinine are estimated calorimetrically using commercial kits.

Test Procedure for Evaluation of Anti-Hyperlipidaemic Activity

The in vivo anti-hyperlipidaemic activity is evaluated in colony-bred adult (3-4 month old) female Sprague-Dawley rats or female retired breeder Sprague-Dawley rats (12-14 months old; parity ≧3). Animals are bilaterally ovariectomized (OVX) under light ether anesthesia and treated with the compound of the present invention, 17-alfa-ethynylestradiol (EE) or the vehicle once daily on days 1-30 post-ovariectomy (day 1: day of bilateral ovariectomy) by the oral route. One group of females is sham operated and treated similarly with the vehicle. Animals of all the groups are autopsied 24 h after the last treatment. At autopsy, about 5 ml blood samples are collected by cardiac puncture from each rat under light ether anesthesia and serum is isolated and stored at −20° C. until analyzed for total cholesterol. The total cholesterol concentration is measured by a timed-end point method using a Beckman Synchron CX autoanalyser. In the reaction, cholesterol estrase hydrolyses cholesterol esters to free cholesterol and fatty acids. Free cholesterol is oxidized to cholestene-3-one and $H_2O_2$ by cholesterol oxidase. Peroxidase catalyses the reaction of $H_2O_2$ with 4-amino antipyrine and phenol to produce a colored quinoneimine product. Absorbance is recorded at 520 nm.

Test Procedure for Evaluation of Antiproliferative/Cytotoxic Activity In Vitro

The procedure is based on the following methods: New colorimetric assay for anticancer drug screening, Skehan et al., J Natn Cancer Inst, 82,1107, 1990 and Feasibility of a high-flux anticancer drug screen using a diverse panel of cultured human tumor cell lines 83,757, 1991.

A fully confluent flask of MCF-7 cells in trypsinized and $10^4$ cells/well are plated in a 96 welled flat bottomed plate in 200 µl Minimum Essential Medium (MEM), pH 7.4 and allowed to attach for 24 h at 37° C. in a humidified $CO_2$ incubator. Subsequently, the compound of invention dissolved in DMSO or ethanol is added at a specified concentration and further incubated for 48 h as before. The cells are then fixed in 50 µl cold 50% TCA and incubated for 1 h at 4° C. The supernatant is discarded and the plate is washed five times with deionized water and air dried. 100 µl of 0.4% (w/v) Sulforhodamine B (SRB) in 1% acetic acid is added to each well and incubated at room temperature for 30 minutes. Unbound SRB is removed by five washes with chilled 1% acetic acid and the plate is air dried. 200 µl of unbuffered 10 mM Tris base is added to solublize the bound stain for 5 minutes at room temperature and O.D. is read at 560 nm in a plate reader. The graph is plotted between O.D. and concentration and $LC_{50}$ is calculated with respect to tamoxifen, which is used as a positive control.

TABLE 2

Antiproliferative/cytotoxic activity in cultured MCF-7 cells

| Compound | $LC_{50}$ (µM) |
| --- | --- |
| Tamoxifen | 14.20 |
| Example number 12 | 18.20 |
| Example number 13 | 17.80 |

Test Procedure for Evaluation of Anti-Cancer Breast Activity In Vivo.

Compound(s) of invention identified on the basis of the above test are evaluated in vivo for anticancer breast activity using the well established and widely used rodent model of hormone responsive breast cancer namely, 7,12-dimethylbenz (a) anthracene (DMBA) induced rat mammary tumor model. Healthy female Sprague-Dawley rats (50-60 days of age) are given a single oral administration of DMBA (180 mg/kg) and the mammary tumor development is monitored by weekly palpation of the mammary tracks. Body weight of the animals is recorded weekly. All animals are used and handled adhering to the Animal Ethics Committee guidelines for humane treatment of animals. The animals have free access to standard rodent pellet diet and safe drinking water and are housed in temperature and photoperiod-controlled animal quarters throughout the experimental period. When palpable mammary tumors develop and reach approximately 0.5 cm in diameter, the tumor bearing rats are grouped and receive oral administration of the test compound at a daily dose of 10 mg/kg body weight for 4 weeks. Tumor incidence, number and area/volume are recorded at the commencement of the treatment and at weekly intervals. The diameter of tumors is measured using calipers and the tumor volume is derived using the formula for sphere volume. The compound is considered active against mammary tumor if, by the end of treatment period, the tumor volume decreases by more than 25% or remains static or when the volume shows less than 25% increase over the pre-treatment volume.

Test Procedure for Evaluation of Post-Coital Antifertility Activity

Adult female rats are caged overnight with coeval males of proven fertility and their vaginal smears are checked on the following morning. The day of presence of spermatozoa in the vaginal smear is taken as day 1 of pregnancy. Mated rats are isolated and randomized into various treatment groups and treated orally with the compound of invention or the vehicle on days 1-7/1-5 post-coitum. Animals of all the groups are autopsied on day 10 post-coitum and number and status of corpora lutea and implantation sites in each rat are recorded. The compounds of the present invention are considered active if there is complete absence of implantations in the uterus of all rats, in comparison to presence of normal implantations in the uterus of rats of vehicle control group.

TABLE 3

Post-coital antifertility efficacy in adult female rats

| Compound | Daily dose (mg/kg) | Treatment schedule (days post-coitum) | % Efficacy |
|---|---|---|---|
| Vehicle | — | 1-7 | — |
| Example number 2 | 0.025 | 1-5 | 67% |
| | 0.05 | 1-5 | 100% |
| | 0.1 | 1-7 | 100% |
| | 0.5 | 1 | 100% |
| | 1 | 1 | 100% |
| Example number 7 | 0.025 | 1-5 | Inactive |
| | 0.05 | 1-5 | 100% |
| | 0.1 | 1-5 | 100% |
| | 0.5 | 1 | 50% |
| | 1 | 1 | 100% |
| Example number 8 | 0.05 | 1-5 | 100% |
| | 0.1 | 1-5 | 100% |
| | 0.5 | 1 | 100% |
| | 1 | 1 | 100% |
| Example number 12 | 0.05 | 1-5 | 50% |
| | 0.1 | 1-7 | 100% |

Test Procedure for Evaluation of Estrogen Agonistic Activity

Twenty-one-day-old immature female rats are bilaterally ovariectomized under light ether anaesthesia and, after post-operative rest for 7 days, are randomized into different treatment groups. Each rat receives the compound of the invention once daily for 3 consecutive days on days 28-30 of age. A separate group of animals receiving only the vehicle for similar duration serves as control. At autopsy 24 h after the last treatment on day 31 of age, vaginal smear of each rat is taken and uterus is carefully excised, gently blotted, weighed and fixed for histology and histomorphometry using image analysis. Premature opening of vagina, cornification of vaginal epithelium, increase in uterine fresh weight, total uterine and endometrial area and uterine luminal epithelial cell height are taken as parameters for evaluation of estrogen agonistic activity in comparison to rats of vehicle control group.

TABLE 4

Increase in uterine weight in immature ovariectomized rats: Percent of OVX + vehicle treatment group

| Compound | Daily dose (mg/kg) | Percent increase |
|---|---|---|
| 17-alfa-Ethynylestradiol | 0.01 | 419 |
| Example number 2 | 0.05 | 38 |
| Example number 7 | 0.05 | 11 |
| Example number 8 | 0.05 | 53 |
| Example number 12 | 0.10 | 120 |

For image analysis in estrogen agonistic activity evaluation studies, paraffin sections (6 μm thick) of the uterus stained with haematoxylin and eosin were analysed microscopically. To determine changes in uterine tissue components, areas of whole uterus and endometrium and the thickness of uterine epithelium were measured using a computer-image analysis system (BioVis, Expert Vision, India). Briefly, microscopic images of uterus acquired through a CCD camera were loaded in to the image analysis program and spatially calibrated against a stage micrometer image taken at the same magnification. Using thresholding and line tools, the regions for measurements were selected and the area ($mm^2$) of whole uterine transection excluding the luminal space, the area ($mm^2$) of the endometrium only, and the thickness (μm) of luminal epithelial lining were measured. Luminal epithelial thickness data was the Average of measurements made at 6 randomly selected sites are taken as parameters for evaluation.

TABLE 5

Estrogen agonistic activity in immature ovariectomized rats: Effect on uterine morphometry

| Compound | Daily dose (mg/kg) | Uterus Total area $mm^2$ | Endometrium Total area $mm^2$ | Endometrium Epithelial cell height μm |
|---|---|---|---|---|
| Vehicle | — | 0.29 | 0.12 | 6.36 |
| 17-alfa-Ethynylestradiol | 0.01 | 1.21 | 0.57 | 33.65 |
| Example number 2 | 0.05 | 0.175 | 0.08 | 8.69 |
| Example number 7 | 0.05 | 0.35 | 0.13 | 6.17 |
| Example number 8 | 0.05 | 0.67 | 0.35 | 17.25 |
| Example number 12 | 0.1 | 0.56 | 0.27 | 15.93 |

Test Procedure for Evaluation of Estrogen Antagonistic Activity

Twenty-one-day-old immature female rats are bilaterally ovariectomized under light ether anaesthesia and after post-operative rest for 7 days, are randomized into different treatment groups. Each rat receives the compounds of the invention and 0.02 mg/kg dose of 17-alfa-ethynylestradiol in 10% ethanol-distilled water once daily for 3 consecutive days on days 28-30 of age. A separate group of animals-receiving only 17-alfa-ethynylestradiol (0.02 mg/kg) in 10% ethanol-distilled water for similar duration are used for comparison. At autopsy on day 31 of age, vaginal smear of each rat is taken and uterus is carefully excised, gently blotted, weighed and fixed for histology and histomorphometry using image analysis. Inhibition in 17-alfa-ethynylestradiol-induced premature opening of vagina, cornification of vaginal epithelium, increase in uterine fresh weight, total uterine and endometrial area and uterine luminal epithelial cell height are taken as parameters for evaluation of estrogen antagonistic activity.

TABLE 6

Percent inhibition in EE induced uterine weight gain in immature ovariectomized rats

| Compound | Daily dose (mg/kg) | Percent inhibition |
|---|---|---|
| Example number 2 | 0.05 | 09 |
| Example number 7 | 0.05 | 31 |
| Example number 8 | 0.05 | 49 |
| Example number 12 | 0.1 | 38 |

Test Procedure for Evaluation of Relative Binding Affinity (RBA) to Estrogen Receptors The relative binding affinity (RBA) of the compounds for estrogen receptor was determined by competition assay, employing $^3H$-estradiol ($^3H$-$E_2$) as the radioligand. The test ligands and $^3H$-$E_2$ were incubated at 4° C. with cytosol estrogen receptors obtained from uteri of immature estradiol-primed (1 μg/rat 24 h before autopsy) 20-21 days old rats. Aliquot of uterine cytosol (200 μl; 2 uteri per ml) prepared in TEA buffer (10 mM Tris, 1.5 mM EDTA, 0.02% sodium azide, pH 7.4) were incubated in duplicate with a fixed concentration of $^3H$-$E_2$ in the absence or presence of various concentrations of the competitor substance dissolved in 30 μl of the TEA buffer containing DMF as co-solvent (final concentration of DMF in the incubation mixture never exceeded 5%) for 18 hrs at 4° C. At the end of this period, dextran coated charcoal (5% Norit 0.5% dextran) suspension in 100 µl of TEA buffer was added to each tube, which were briefly vortexed and allowed to stand for 15 minutes at 4° C. The mixture was centrifuged at 800 g for 10 minutes and the supernatants counted for radioactivity in 10 ml of a dioxane-based scintillation fluid. RBA of the text compound was computed from a graph plotted between percent bound radioactivity verses log concentration of the test substance. At 50% inhibition, log of the competitor concentration relative to that of 17-beta-estradiol, gave the affinity of the test compound to estrogen receptor relative to estradiol. This when multiplied with 100 gave the percentage value designated as RBA.

TABLE 7

Relative binding affinity (RBA) to estrogen receptors

| Compound | RBA |
| --- | --- |
| 17-beta-Estradiol | 100 |
| Example number 2 | 5.45 |
| Example number 8 | 6.6 |

The derivates of the instant application are novel in nature and are found to have the aforementioned activities. These activities are absent in the basic structure of the compound of formula I. Thus, the invention of the instant Application is both novel and non-obvious.

The invention claimed is:
1. Compounds of the following:
(1) (3R,4R)-2,2-Dimethyl-7-methoxy-4-(4-[{(2R)-3-methylamino-2-hydroxy}propyloxy]phenyl)-3-phenyl-chroman;
(2) (3R,4R)-2,2-Dimethyl-7-methoxy-4-(4-[{(2R)-3-ethylamino-2-hydroxy}propyloxy]phenyl)-3-phenyl-chroman;
(3) (3R,4R)-2,2-Dimethyl-7-methoxy-3-phenyl-4-(4-[{(2R)-3-propylamino-2-hydroxy}propyloxy]phenyl) chroman;
(4) (3R,4R)-4-(4-[{(2R)-3-Butylamino-2-hydroxy }propyloxy]phenyl)-2,2-dimethyl-7-methoxy-3-phenyl-chroman;
(5) (3R,4R)-2,2-Dimethyl-7-methoxy-4-(4-[{(2R)-3-pentylamino-2-hydroxy}propyloxy]phenyl)-3-phenylchroman;
(6) (3R,4R)-2,2-Dimethyl-4-(4-[{(2R)-3-dimethylamino-2-hydroxy}propyloxy]phenyl)-7-methoxy-3-phenyl-chroman;
(7) (3R,4R)-4-(4-[{(2R)-3-Diethylamino-2-hydroxy}propyloxy]phenyl)-2,2-dimethyl-7-methoxy-3-phenylchroman;
(8) (3R,4R)-2,2-Dimethyl-4-(4-[{(2R)-3-dipropylamino-2-hydroxy}propyloxy]phenyl)-7-methoxy-3-phenyl-chroman;
(9) (3R,4R)-4-(4-[{(2R)-3-Dibutylamino-2-hydroxy}propyloxy]phenyl)-2,2-dimethoxy-3-phenyl-chroman;
(10) (3R,4R)-2,2-Dimethyl-4-(4-[{(2R)-3-dipentylamino-2-hydroxy}propyloxy]phenyl)-7-methoxy-3 -phenylchroman;
(11) (3R,4R)-2,2-Dimethyl-7-methoxy-3-phenyl-4-(4-[{(2R)-3-pyrrolidino-2-hydroxy}propyloxy]phenyl)-chroman;
(12) (3R,4R)-2,2-Dimethyl-7-methoxy-3-phenyl-4-(4-[{(2R)-3-piperidino-2-hydroxy}propyloxy]phenyl)-chroman;
(13) (3R,4R)-2,2-Dimethyl7-methoxy-3-phenyl-4-(4-[{(2R)-3-morpholino-2-hydroxy}propyloxy]phenyl)-chroman;
(14) (3R,4R)-2,2-Dimethyl-7-methoxy-3-phenyl-4-(4-[{(2R)-3-piperazino-2-hydroxy}propyloxy]phenyl)-chroman;
(15) (3R,4R)-2,2-Dimethyl-7-methoxy-3-phenyl-4-(4-[{(2R)-3-cyclohexylamino-2-hydroxy}propyloxy]phenyl)-chroman;
(16) (3R,4R)-2,2-Dimethyl-7-methoxy-4-(4-[{(2S)-3-methylamino-2-hydroxy}propyloxy]phenyl)-3-phenyl-chroman;
(17) (3R,4R)-2,2-Dimethyl-7-methoxy-4-(4-[{(2S)-3-ethylamino-2-hydroxy}propyloxy]phenyl)-3-phenyl-chroman;
(18) (3R,4R)-2,2-Dimethyl-7-methoxy-3-phenyl-4-(4-[{(2S)-3-propylamino-2-hydroxy}propyloxy]phenyl)-chroman;
(19) (3R,4R)-4-(4-[{(2S)-3-Butylamino-2-hydroxy}propyloxy]phenyl)-2,2-dimethyl-7-methoxy-3-phenylchroman;
(20) (3R,4R)-2,2-Dimethyl-7-methoxy-4-(4-[{(2S)-3-pentylamino-2-hydroxy}propyloxy]phenyl)-3-phenyl-chroman;
(21) (3R,4R)-2,2-Dimethyl-4-(4-[{(2S)-3-dimethylamino-2-hydroxy}propyloxy]phenyl)-7-methoxy-3-phenylchroman;
(22) (3R,4R)-4-(4-[{(2S)-3-Diethyiamino-2-hydroxy}propyloxy]phenyl)-2,2-dimethyl-7-methoxy-3-phenylchroman;
(23) (3R,4R)-2,2-Dimethyl-4-(4-[{(2S)-3-dipropylamino-2-hydroxy}propyloxy]phenyl)-7-methoxy-3 -phenyl-chroman;
(24) (3R,4R)-4-((4-[{(2S)-3-Dibutylamino-2-hydroxy}propyloxy]phenyl)-3-phenyl) -2,2-dimethoxy-3-phenylchroman;
(25) (3R,4R)-2,2-Dimethyl-4-(4-[{(2S)-3-dipentylamino-2-hydroxy}propyloxy]phenyl)-7-methoxy-3-phenylchroman;
(26) (3R,4R)-2,2-Dimethyl-7-methoxy-3-phenyl-4-(4-[{(2S)-3-pyrrolidino-2-hydroxy}propyloxy]phenyl)-chroman;
(27) (3R,4R)-2,2-Dimethyl-7-methoxy-3-phenyl-4-(4-[{(2S)-3-piperidino-2-hydroxy}propyloxy]phenyl)-chroman;
(28) (3R,4R)-2,2-Dimethyl-7-methoxy-3-phenyl-4-(4-[{(2S)-3-morpholino-2-hydroxy}propyloxy]phenyl)-chroman;
(29) (3R,4R)-2,2-Dimethyl-7-methoxy-3-phenyl-4-(4-[{(2S)-3-piperazino-2-hydroxy}propyloxy]phenyl)-chroman; and
(30) (3R,4R)-2,2-Dimethyl-7-methoxy-3-phenyl-4-(4-[{(2S)-3-cyclohexylamino-2-hydroxy}propyloxy]phenyl)-chroman.

2. A process for the preparation of compounds of formula I,

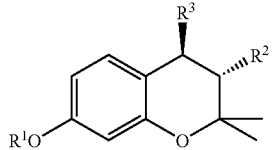

(1)

wherein:
$R^1$ is H or C1-C6 alkyl; C3-C7 cycloalkyl:
$R^2$ is phenyl, optionally substituted with 1 to 5 substituents independently selected from the group comprising OH, C1-C6 -alkyl, halogen, nitro, cyano, SH, $SR^4$, trihalo-C1-C6 -alkyl, C1-C6 alkoxy and phenyl, wherein $R^4$ is C1-C6 alkyl;
$R^3$ is phenyl substituted with $OR^5$ wherein $R^5$ has the formula (II) (III) or (IV)

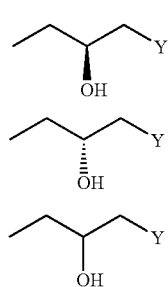 (II)

(III) 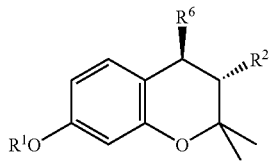

(IV) 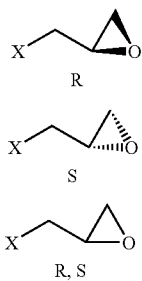

wherein Y is chosen from $NHR^4$, $NR^4_2$, $NHCOR^4$, $NHSO_2R^4$, $CONHR^4$, $CONR^4$, $CONR^4_2$, COCH, $COOR^4$, $SO_2R^4$, $SOR^4$, $SONHR^4$, $SONR^4_2$, a C3-C7 heterocyclic ring, saturated or unsaturated, containing one or two heteroatoms independently selected from the group consisting of O, S and N, optionally being substituted with 1 to 3 substituents independently selected from the group comprising H, OH, halogen, nitro, cyano, SH, $SR^4$, trihalo-C1-C6-alkyl, C1-C6-alkyl, and C1-C6 -alkoxy, preferably including $NHR^4$, $NR_2^4$, or a nitrogen heterocycle, wherein $R^4$ is as defined above;

said process comprising steps of:

I. reacting a compound of formula V

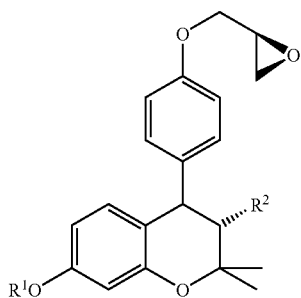 (V)

in which substituents $R^2$ and $R^6$ are arranged in the (3R,4R) configuration: wherein $R^1$ and $R^2$ are as defined in formula and $R^6$ is phenyl substituted with a hydroxy substituents at C2, C3 or C4, with a compound of formula VI, VII, VIII, neat or in an aprotic solvent which includes dimethylsulphoxide, dimethylformamide in the presence of a base including $K_2CO_3$ at temperature ranging between 50 to 120°C.,

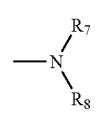 (VI)

(VII)

(VIII)

II. obtaining compounds of structure IX (a-c) wherein $R^1$ and $R^2$ are as defined in formula 1,

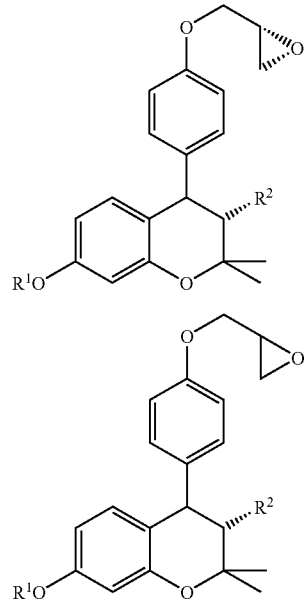 (IXa)

(IXb)

(IXc)

III. reacting compound of formula IX a-c with a nucleophile including an amine of formula X:

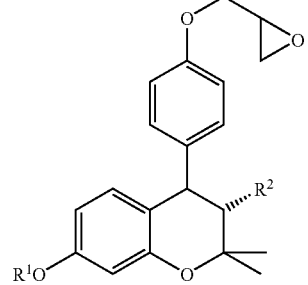 (X)

wherein $R^7$ and $R^8$ are individually hydrogen, C1-C6-alkyl which includes straight chain as well as branched alkyl groups including methyl, ethyl, propyl, isopropyl, butyl, isobutyl C1-C6-cycloalkyl which includes cyclopropane, cyclobutane, cyclopentane, cyclohexane or form a C3-C7 heterocyclic ring, saturated or unsaturated containing one or two heteroatoms independently selected from the group comprising O, S and N, optionally being substituted with 1,2,3 substituents independently selected from the group comprising H, OH, halogen, nitro, cyano, SH, $SR^4$, trihalo-C1-C6-alkyl, C1-C6-alkyl and C1-C6-alkoxy, wherein $R^4$ is defined above, either neat or in the presence of organic solvent including benzene, dimethylsulphoxide, dimethylformamide, and IV. obtaining compounds of formula X1 a-c, optionally converting the amino derivative into their corresponding salts including HCL, fumerate, citrate by treating the free base with the corresponding acid,

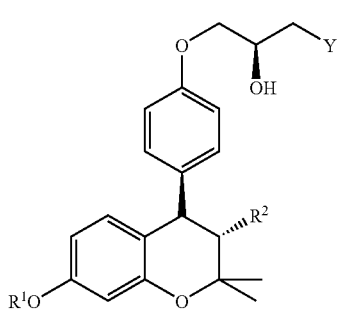 (XI a)

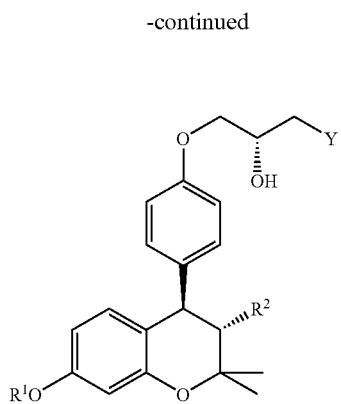
(XI b)
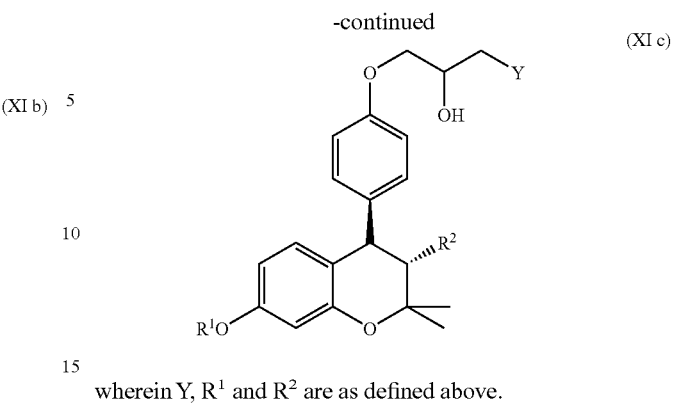
wherein Y, $R^1$ and $R^2$ are as defined above.
* * * * *